US010188602B2

(12) United States Patent
Baillie et al.

(10) Patent No.: US 10,188,602 B2
(45) Date of Patent: Jan. 29, 2019

(54) BIOERODIBLE IMPLANT FOR LONG-TERM DRUG DELIVERY AND ASSOCIATED METHODS OF MANUFACTURE AND USE

(71) Applicant: Gesea Biosciences Inc., Lynnwood, WA (US)

(72) Inventors: John H. Baillie, Glen Ellen, CA (US); Ruth Baillie, Glen Ellen, CA (US); George Blouin, Lynnwood, WA (US); Newsha Farahani, Issaquah, WA (US); Christopher Marx, Mukilteo, WA (US)

(73) Assignee: GESEA BIOSCIENCES INC., San Luis Obispo, CA (US)

( * ) Notice: Subject to any disclaimer, the term of this patent is extended or adjusted under 35 U.S.C. 154(b) by 0 days.

(21) Appl. No.: 15/720,921

(22) Filed: Sep. 29, 2017

(65) Prior Publication Data
US 2018/0085305 A1 Mar. 29, 2018

Related U.S. Application Data

(60) Provisional application No. 62/401,167, filed on Sep. 29, 2016.

(51) Int. Cl.
*A61F 6/08* (2006.01)
*A61F 6/22* (2006.01)
(Continued)

(52) U.S. Cl.
CPC .............. *A61K 9/0024* (2013.01); *A61F 6/08* (2013.01); *A61F 6/22* (2013.01); *A61K 9/0002* (2013.01);
(Continued)

(58) Field of Classification Search
None
See application file for complete search history.

(56) References Cited

U.S. PATENT DOCUMENTS

| 4,957,119 A | 8/1990 | de Nijs |
| 5,035,891 A | 7/1991 | Runkel et al. |

(Continued)

FOREIGN PATENT DOCUMENTS

WO     1990/010437 A1     9/1990

OTHER PUBLICATIONS

International Search Report and Written Opinion of the International Searching Authority of PCT/US2017/054466, dated Feb. 22, 2018.

(Continued)

*Primary Examiner* — Bethany P Barham
*Assistant Examiner* — Dominic Lazaro
(74) *Attorney, Agent, or Firm* — Dianne E. Reed; VLP Law Group LLP

(57) ABSTRACT

A drug delivery system is provided in the form of a controlled release, bioerodible pellet for subdermal implantation. The pellet is bioerodible, and provides for the sustained release of a pharmacologically active agent over an extended time period. As such, the drug delivery system finds significant utility in chronic drug administration. Bioerosion products are water soluble, bioresorbed, or both, obviating the need for surgical removal of the implant. Methods for manufacturing and using the drug delivery system are also provided.

29 Claims, 17 Drawing Sheets

(51) Int. Cl.

| | | |
|---|---|---|
| A61K 9/00 | (2006.01) | |
| A61K 31/167 | (2006.01) | |
| A61K 31/192 | (2006.01) | |
| A61K 31/325 | (2006.01) | |
| A61K 31/57 | (2006.01) | |
| A61K 31/593 | (2006.01) | |
| A61K 47/10 | (2017.01) | |
| A61K 47/12 | (2006.01) | |
| A61K 47/24 | (2006.01) | |
| A61K 47/28 | (2006.01) | |
| A61K 31/567 | (2006.01) | |
| A61F 2/30 | (2006.01) | |
| A61L 27/54 | (2006.01) | |
| A61L 27/58 | (2006.01) | |

(52) U.S. Cl.
CPC .......... *A61K 31/167* (2013.01); *A61K 31/192* (2013.01); *A61K 31/325* (2013.01); *A61K 31/567* (2013.01); *A61K 31/57* (2013.01); *A61K 31/593* (2013.01); *A61K 47/10* (2013.01); *A61K 47/12* (2013.01); *A61K 47/24* (2013.01); *A61K 47/28* (2013.01); *A61F 2002/30677* (2013.01); *A61L 27/54* (2013.01); *A61L 27/58* (2013.01); *A61L 2300/404* (2013.01)

(56) References Cited

U.S. PATENT DOCUMENTS

| | | | |
|---|---|---|---|
| 5,039,660 A | 8/1991 | Leonard et al. | |
| 5,137,669 A | 8/1992 | Leonard et al. | |
| 5,543,156 A | 8/1996 | Roorda et al. | |
| 5,660,848 A | 8/1997 | Moo Young | |
| 5,688,519 A | 11/1997 | Leonard | |
| 5,888,533 A | 3/1999 | Dunn | |
| 5,945,115 A | 8/1999 | Dunn et al. | |
| 6,120,789 A | 9/2000 | Dunn | |
| 8,173,148 B2 | 5/2012 | Dadey | |
| 8,357,388 B2 | 1/2013 | McKay | |
| 8,722,037 B2 | 5/2014 | Veenstra et al. | |
| 9,283,212 B2 | 3/2016 | O'Neil | |
| 9,345,686 B2 | 5/2016 | De Graaf et al. | |
| 9,399,018 B2 | 7/2016 | Hudson | |
| 2006/0003008 A1 | 1/2006 | Gibson et al. | |
| 2008/0096910 A1 | 4/2008 | Guarnieri | |
| 2008/0112892 A1 | 5/2008 | Veenstra et al. | |
| 2011/0086083 A1* | 4/2011 | Biggs | A61K 9/0024 424/424 |
| 2014/0342985 A1 | 11/2014 | Gibson et al. | |
| 2014/0343080 A1 | 11/2014 | Siegel et al. | |
| 2016/0220498 A1 | 8/2016 | Soni et al. | |

OTHER PUBLICATIONS

Singh et al. Biodegradable norethindrone (NET:cholesterol) contraceptive implants: phase II-A: clinical study in women. Contraception. Jan. 1997;55(1):23-33.

Darney et al. Clinical evaluation of the Capronor contrac-.flptive implant: preliminary report. Am J Obstet Gynecol. May 1989;160(5 Pt 2):1292-5. abstract.

Darney et al. Subdermal progestin implant contraception. Curr Opin Obstet Gynecol. Aug. 1991;3(4):470-6. abstract.

International Search Report and Written Opinion of the International Searching Authority, PCT/US2017-054436, dated Dec. 26, 2017.

Raymond et al.,"Contraceptive Efficacy, Pharmacokinetics, and Safety of Annuelle® Biodegradable Norethindrone Pellet Implants," Fertility and Sterility (1996), 66(6): 954-961.

Gupta et al., "Multicenter Clinical Trial of Implanted Norethindrone Pellets for Long-Acting Contraception in Women," Contraception (1984) 30(3):239-252.

Joshi et al., "Phase I Comparative Clinical Trial with Subdermal Implants—Bioabsorbable Levonorgestrel or Norethisterone Pellet Fused with Cholesterol," Contraception (1985)31(1):71-82.

Guarnieri, "Subcutaneous implants for long-acting drug therapy in laboratory animals may generate unintended drug reservoirs," J. Pharm. Bioallied Sci. (2014) 6(1):38-42.

* cited by examiner

Mean Patient Serum NET Levels

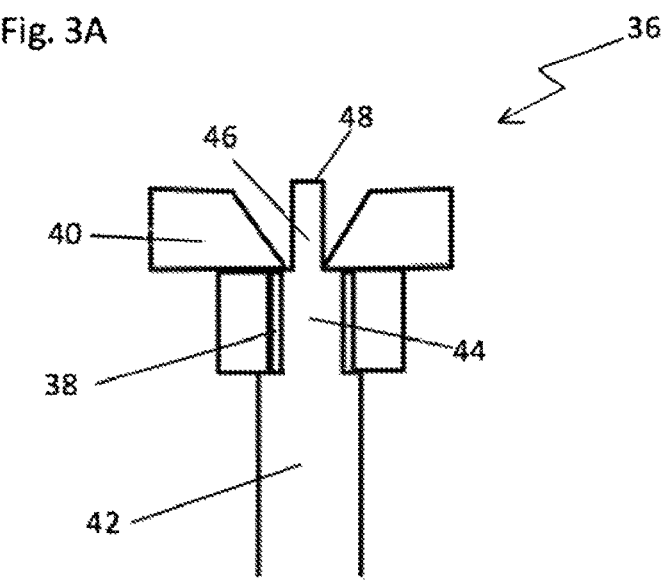
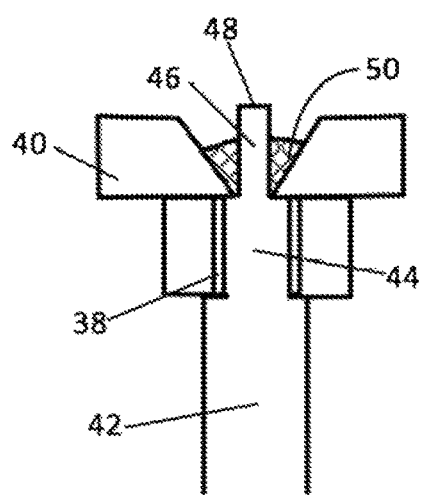
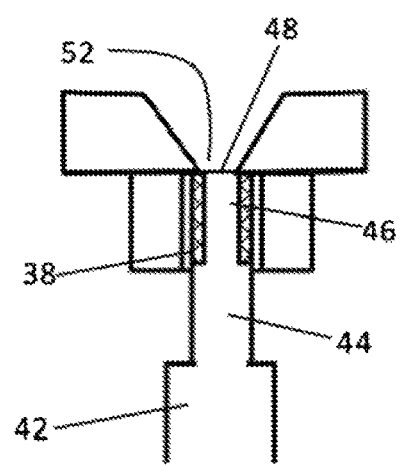

BIOERODIBLE IMPLANT FOR LONG-TERM DRUG DELIVERY AND ASSOCIATED METHODS OF MANUFACTURE AND USE

CROSS-REFERENCE TO RELATED APPLICATIONS

This application claims priority under 35 U.S.C. § 119(e)(1) to provisional U.S. Patent Application Ser. No. 62/401,167, filed Sep. 29, 2016, the disclosure of which is incorporated by reference herein.

BACKGROUND OF THE INVENTION (1) Technical Field:

The invention relates generally to controlled release drug delivery systems, and more particularly relates to bioerodible implants for controlled release of a pharmacologically active agent over an extended time period. The invention finds utility in the fields of drug delivery, pharmaceuticals, medicine, and public health.

(2) Description of Related Art:

Many individuals must take medication on a regular basis for a significant period of time. Such chronic pharmacotherapy is necessary for many different types of drugs prescribed in a wide variety of contexts, ranging from antidepressant and antipsychotic medications taken several times a day to prevent a serious mental health setback, to antiretroviral "cocktails" that require an ongoing and complicated dosage regimen to effectively treat a potentially fatal disease such as Acquired Immune Deficiency Syndrome ("AIDS"). A lack of patient compliance in such cases, including even a relatively small divergence from a prescribed dosage regimen, can adversely affect a patient's health and well being and even jeopardize a patient's life.

Furthermore, there are numerous medications that can diminish a person's ability to think clearly or adversely affect short term memory, in turn impacting on a patient's ability to follow a prescribed dosage regimen. It is well known, for example, that many life-saving cancer drugs are associated with so-called "Chemotherapy-Related Cognitive Impairments," sometimes referred to as "chemo brain" or "chemo fog," which reduces the likelihood that the cancer patient can adhere to a required dosage regimen.

A reliable drug delivery system for chronic administration of one or more pharmacologically active agents could overcome the problems noted above, eliminating the need for rigorous compliance with a prescribed drug dosage regimen.

Such a system would also be useful in the long-term, controlled release delivery of active agents that are commonly administered orally, as a delivery system for continuously administering a drug over a period of months, or even years, would not involve oral administration. Superior long-term drug delivery systems would thus be useful with drugs that exhibit low oral bioavailability as a result of first-pass metabolism or incomplete absorption. Drugs that exhibit a significant first pass effect include well known and often prescribed drugs such as imipramine, propranolol, buprenorphine, diazepam, cimetidine, and nitroglycerine, among others.

An effective long-term controlled release delivery system would also be useful to administer drugs that are usually given orally, but where oral administration often results in moderate to severe gastrointestinal ("GI") side effects. For example, oral administration of nonsteroidal anti-inflammatory agents (commonly known as "NSAIDs") is associated with numerous GI side effects that include nausea and vomiting, dyspepsia, gastric ulceration, gastric bleeding, and diarrhea. With NSAIDS, these GI side effects are due to the acidity of the drugs and to their inhibition of COX-1 and/or COX-2, a mechanism of action that reduces the amount of protective prostaglandins synthesized in the GI tract. Antiepileptic drugs, pain drugs, and numerous other drugs that are commonly administered via the oral route are also known to result in a multitude of gastrointestinal side effects.

The idea of using implantable pellets to provide for controlled release of an active agent over an extended time period is known. In the area of contraception, for instance, drug delivery implants have been proposed as systems that would eliminate the need for daily dosing (as is required with oral contraceptive agents) and provide reliable contraceptive protection for an extended time period, e.g., a year, two years, three years, or even longer. An ideal long-term contraceptive agent would also be "forgettable" insofar as its effectiveness would not depend on user compliance each day or at each coital act; removable before complete absorption, for women who decide to terminate use of birth control; and biodegradable, so that removal is not required.

Most of the work on contraceptive implants to date has involved the use of aliphatic polyesters, including polylactic acid (PLA), polyglycolic acid (PGA), polycaprolactone (PCL) and the copolymer of PLA and PGA, poly (lactic-co-glycolic acid) (PLGA); see Pitt et al. (1981) *NIDA Res. Monogr.* 28:232-53. Such materials have been viewed as attractive candidates because their degradation products are naturally occurring metabolites, i.e., lactic and glycolic acid. A polycaprolactone-based contraceptive implant, Capronor™, was developed in the 1980s to release levonorgestrel for a period in the range of 12 to 18 months and then degrade. The product was ultimately abandoned, however, because of skin irritation experienced by study participants, stability problems during storage, and a long release tail, explained infra.

More recently, long-term controlled release implants have been developed for the administration of etonogestrel (Implanon®, as well as the newer radio-opaque version, Nexplanon®, from Merck & Co.). See Maddox et al. (2008) *P&T* 33(6):337-347, the prescribing information for Implanon and Nexplanon, and U.S. Pat. Nos. 4,957,119, 8,722,037 and 8,888,745. Like many other implants, however, Implanon and Nexplanon must be surgically removed once the active agent is depleted. The need for surgical removal of an implant is inconvenient and potentially risky; issues can arise with the formation of fibrous tissue around the implant, the failure to locate implants that may have been inserted too deeply, pain, tissue damage, local infection, and nerve damage.

In addition, many controlled release implants are associated with a long "tail period" after much of the active agent has been released, in which the implant is still releasing active agent but at a sub-effective level; see, e.g., Raymond et al. (1996) *Fertil. Steril.* 66(6):954-61. In the aforementioned study, involving a biodegradable implant, the dosage of the contraceptive agent fell below the minimum effective level for some time, in some cases for as long as 18 months. This is an unacceptably long time period during which contraceptive agent is still being delivered but at a dosage that is too low to provide a contraceptive effect. Other implants that are bioerodible have also resulted in significant tail period.

There is, accordingly, an ongoing need in the art for an implantable drug delivery system that provides for controlled release of an active agent throughout an extended drug delivery time period. An ideal controlled release implant would be (1) bioerodible, thereby obviating the need for surgical removal, (2) composed of non-toxic, naturally occurring materials, (3) simple, inexpensive, and straightforward to manufacture, without need for many steps, complicated equipment, toxic reagents, or a great deal of time, and (4) physically and chemically stable during storage, handling, sterilization, handling, and a possible early removal procedure. In addition, an ideal drug delivery implant would provide for controlled release of an active agent at an effective level over an extended time period, as is necessary with chronic pharmacotherapy. The ideal implant would also have a reduced tail period relative to those observed with earlier implants.

BRIEF SUMMARY OF THE INVENTION

Accordingly, the invention is directed to the aforementioned need in the art and, in one embodiment, provides a drug delivery system in the form of a subdermally implantable pellet that provides for controlled, sustained release of a pharmacologically active agent throughout an extended drug delivery time period. The pellet comprises an amount of an active agent which, following subdermal implantation of at least one of the pellets into an individual, results in a serum level of the active agent sufficient to provide efficacy during the extended drug delivery time period. The pellet is bioerodible in situ, so that there is no need for surgical removal of the pellet at the end of the drug delivery period. That is, any bioerosion products are water soluble, bioresorbable, or both, so as to dissolve in or be absorbed by the body.

In one aspect of this embodiment, the drug delivery system is comprised of more than one pellet.

In another aspect of this embodiment, the drug delivery system comprises two to six pellets, e.g., four or five pellets.

In another aspect of this embodiment, the pellet as a whole is lipophilic, meaning that the total of any hydrophilic components represent less than 50 wt. % of the pellet.

In a related aspect, the total of any hydrophilic components represents less than 45 wt %, less than 40 wt. %, less than 35 wt. %, less than 30 wt. %, less than 25 wt. %, less than 20 wt. %, less than 15 wt. %, less than 10 wt. %, or less than 5 wt. % of the pellet. It will thus be appreciated that the pellet may be substantially free of hydrophilic components.

In another aspect of this embodiment, the pellet comprises a solid at the temperature in the range of about about 35° C. to about 40° C. This ensures that the pellet will be in substantially solid form in the body and under storage conditions. In a preferred embodiment, a hot melt pellet manufacturing method is employed, as described infra, in which case the pellet composition should be flowable at a selected temperature in the range of about 50° C. to about 250° C.

In an additional aspect of this embodiment, the pellet contains an excipient composition that includes at least one excipient. Each pellet excipient should be (a) a water-soluble and/or bioresorbable compound, or (b) transformed in situ to water-soluble and/or bioresorbable species, i.e., during pellet bioerosion, or both (a) and (b). In a related aspect of this embodiment, pellet excipients are selected from naturally occurring materials, where the naturally occurring materials may be obtained from a biological source or chemically synthesized in whole or in part.

In another aspect of this embodiment, the pellet has an elongated form. For example, the pellet may comprise a rod-shape dosage form that may be substantially cylindrical.

In another aspect of this embodiment, the pellet is monolithic, comprising a substantially homogeneous matrix with the active agent dispersed therein.

In another aspect of this embodiment, the pellet is composed of two or more discrete regions each having a different composition, e.g., compositions that differ with respect to components, component amount, component concentration, or the like. For example, the pellet may be composed of two regions, with a first region containing the active agent and the second region containing only inactive ingredients. As another example, the first region and the second region may both contain the same active agent but with the agent present in different amounts and/or at different concentrations. As a further example, the first and second regions may contain two different active agents.

In a related aspect, the pellet is composed of a core-and-shell type of dosage form, where the first discrete region is the core and the second discrete region is the shell. With an elongated dosage form, the first region may be an inner core having a length, a surface along the length, a first end, and a second end, and the second region may be an outer shell enclosing the surface of the inner core along its length but not the first end or the second end, such that the core has an exposed surface area at the first and second ends. This type of structure may be one wherein: at least about 80 wt. % (e.g., at least about 90 wt. %, including 100%) of the active agent in the pellet is in the core (referred to herein as a "core-type" pellet); at least about 80 wt. % (e.g., at least about 90 wt. %, including 100%) of the active agent in the pellet is in the shell (referred to herein as a "shell-type" pellet); or active agent is present in both the core and the shell with greater than about 20 wt. % of the active agent present in each region.

In another aspect of this embodiment, the extended drug delivery time period includes an effective drug delivery time period, during which the active agent is released at a dosage sufficient to provide therapeutic efficacy, where the effective drug delivery time period is in the range of about three months to about four years, e.g., about six months to about four years; about six months to about three years; or about one year to about three years, such as about 18 months.

In another aspect of this embodiment, the extended drug delivery time period includes two time periods, a first time period that is an effective drug delivery period as defined in the preceding paragraph, and a subsequent, second time period that is a sub-effective drug delivery period during. That is, the pellet releases the active agent during the first, "effective drug delivery period" at a dosage sufficient to provide therapeutic efficacy, but thereafter, during the "sub-effective drug delivery period," the pellet continues to release the active agent but at a dosage that is less than sufficient to provide therapeutic efficacy (where effective and sub-effective dosages correlate with effective and sub-effect serum levels, respectively). The sub-effective drug delivery period, during which the pellet continues to release the active agent but at a dosage below an effective therapeutic dosage, is sometimes referred to as a "tail period" and, in a preferred embodiment, is at most about 12 months. In a related aspect of this embodiment, the tail period is at most about 9 months.

In another embodiment, one or more aspects of the pharmacokinetic profile of the subdermally implantable pellet are selected and "tuned" during manufacture, using at least one pellet property selected from width, length, diameter, surface area, size, composition, hardness, and degree of crystallinity.

In a related aspect of this embodiment, the pellet includes a release rate controlling agent as an excipient, wherein the release rate controlling agent has a water solubility effective to increase the release rate of the active agent from the pellet or to decrease the release rate of the active agent from the pellet, relative to the release rate of the active agent from the pellet in the absence of the release rate controlling agent.

In another related aspect of this embodiment, the pellet includes a softening agent as an excipient. The selection of softening agent, the amount of the softening agent, or both, are selected so that the overall hardness of the pellet is as desired, e.g., for purposes of implantation, palpation, or the like. In a further related aspect of this embodiment, the softening agent is a crystallinity modulator.

In another related aspect of this embodiment, the active agent and has an aqueous solubility of less than about 50 mg/mL.

In a related aspect of this embodiment, the active agent is selected from an analgesic agent; an anti-anxiety agent; an anti-arthritic agent; an anti-asthmatic agent; an anticancer agent; an anticholinergic agent; an anticholinesterase; an anticonvulsant; an antidepressant; an antidiabetic agent; an antidiarrheal agent; an anti-emetic agent; an antihistamine; an antihyperlipidemic agent; an anti-infective agent; an anti-inflammatory agent; an antimigraine agent; an anti-obesity agent; an antipruritic agent; an antipsychotic agent; an antispasmodic agent; an agent for treating a neurodegenerative disease; a cardiovascular medicament; a diuretic agent; a gastrointestinal medication; a hormone or antihormone; a hypnotic agent; an immunosuppressive agent; a leukotriene inhibitor; a narcotic agonist or antagonist; a neurotransmitter; nicotine; a nucleic acid; a peptide drug; a nutrient; a sympathomimetic agent; a thrombolytic agent; a vasodilator; or a combination thereof In further related aspects of this embodiment, the active agent comprises an antipsychotic agent; an anti-inflammatory agent, e.g., a non-steroidal anti-inflammatory agent; a gastrointestinal medication, e.g., a proton pump inhibitor; an anticancer agent, e.g., an anti-metabolite, an anti-microtubule agent, a cytotoxic antibiotic, a topoisomerase inhibitor, an aromatase inhibitor, a GnRH analogue, a hormone receptor antagonist, a hormonal agent, an anti-angiogenic agent, or an anti-metastatic agent; an anti-infective agent, e.g., an antibiotic, an antiviral agent, an antifungal agent, or an antiparasitic agent; a cardiovascular medicament, e.g., an antiarrhythmic agent, an antihypertensive agent, or an anti-anginal agent; an agent for treating a neurodegenerative disorder; a phytonutrient; a vitamin; or a combination thereof.

In another embodiment, the invention provides a method for administering a pharmacologically active agent to a subject in a sustained release manner over an extended drug delivery time period, where the method involves subdermally implanting a drug delivery system as described above into the subject and allowing the drug delivery system to remain in place throughout the extended drug delivery time period.

The invention also provides a method for making a monolithic pellet for controlled release of a pharmacologically active agent, comprising: comprising:

(a) providing (i) an elongated pin having a substantially cylindrical upper segment terminating in a pin tip, (ii) a pelleting tube having an upper tube opening, an opposing lower tube opening, an inner surface, and an inner diameter sized to provide a sealing fit between the inner surface and the upper segment of the pin, and (iii) a funnel having an outlet aligned with the upper tube opening;

(b) inserting the pin tip into the lower tube opening and moving the pin upward through the tube toward the funnel until the pin tip reaches the upper tube opening;

(c) placing a molten pellet composition into the funnel, the composition containing the pharmacologically active agent;

(d) partially withdrawing the pin from the tube through the lower tube opening such that the pin tip is lowered a selected distance from the upper tube opening, thereby drawing the pellet composition into the tube; and (e) allowing the pellet composition to cool within the tube so as to form a pellet having a pellet length corresponding to the selected distance and a pellet diameter defined by the inner diameter.

A method for making a core-and-shell type of pellet for controlled release of a pharmacologically active agent, the method comprising:

(a) providing (i) an elongated pin comprising two axially aligned, substantially cylindrical adjacent segments of different diameters, with a wider lower segment and a narrower upper segment terminating in a pin tip, (ii) a pelleting tube having an upper tube opening, an opposing lower tube opening, an inner surface, and an inner diameter sized to provide a sealing fit between the inner surface and the lower segment of the pin, and (iii) a funnel having an outlet aligned with the upper tube opening;

(b) inserting the pin tip into the lower tube opening and moving the pin upward through the tube toward the funnel until the pin tip and upper pin segment protrude from the upper tube opening into the funnel, thereby bringing the lower pin segment within the tube;

(c) placing a molten shell composition in the funnel;

(d) gradually withdrawing the lower segment from the tube through the lower tube opening, thereby lowering the upper segment into the tube and simultaneously drawing the shell composition into a concentric space between the upper segment and the inner surface of the tube;

(e) allowing the shell composition to cool and harden into a shell formed around the upper segment within the concentric space;

(f) placing a molten core composition into the funnel; and (g) gradually lowering the upper segment within the tube in a manner that draws the core composition into the shell, wherein the shell composition and/or core composition contain a pharmacologically active agent.

The core-and-shell pellet thus formed is allowed to cool and harden within the tube. The pin is then completely withdrawn and the pellet can be removed from the tube.

BRIEF DESCRIPTION OF THE DRAWINGS

FIG. 3A schematically illustrates a pellet manufacturing assembly used to make a core-and-shell type pellet of the invention; FIG. 3B illustrates the core-and-shell type pellet manufacturing assembly of FIG. 3A with the shell composition having been introduced into the funnel above the pelleting tube; FIG. 3C illustrates the core-and-shell type pellet manufacturing assembly of FIG. 3B with the shell material has been drawn down into a concentric space within the pelleting tube.

FIG. 23 shows the dissolution of monolithic pellets and core-type pellets made with cholecalciferol, as described in Example 11. while

FIG. 25 provides the release profiles for each of the core pellets prepared in Examples 9-12, i.e., for naproxen, methocarbamol, cholecalciferol, and acetaminophen, while

DETAILED DESCRIPTION OF THE INVENTION

Figure 1:
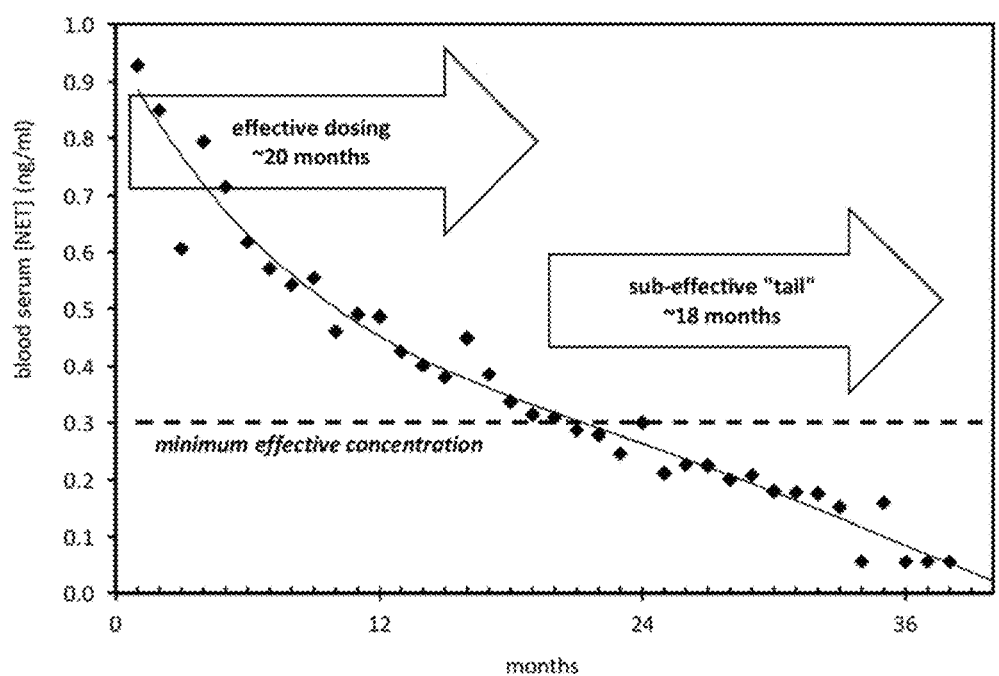
FIG. 1 (PRIOR ART) is a graph showing the extended time period during which an implanted norethindrone pellet was found to release sub-effective but detectable concentrations of the active agent (adapted from Raymond et al. (1996) *Fertil. Steril.* 66(6):954-61).

I. Definitions and Terminology:

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise. Thus, for example, "an active agent" refers not only to a single active agent but also to two or more active agents that may or may not be combined in a mixture; "an excipient" refers to a single excipient or two or more excipients, which, again, may or may not be combined in a mixture; and the like.

The term "bioerodible" is used herein in a manner synonymous with "biodegradable," and includes any mechanism that may contribute to the gradual reduction in mass of an implanted pellet throughout an extended drug delivery period. Thus, a bioerodible pellet may degrade as a result of in vivo forces interacting with the pellet surface such as shear forces; cellular action, e.g., endocytosis and cell-mediated dispersion of microscopic particles released from the pellet during cell migration; and gradual dissolution of one or more pellet components. Throughout this disclosure and claims, the use of the term "bioerodible" to characterize a subdermally implantable pellet of the invention also indicates that the pellet bioerodes in situ in a manner that obviates the need for surgical removal after completion of drug release (although earlier removal may sometimes be desirable for one reason or another), insofar as all pellet bioerosion products are either water soluble, bioresorbable, or both. Accordingly, the term "bioerodible," in a first instance, refers to a completely bioerodible pellet, which may be, for example, a pellet entirely composed of an active agent that is gradually released in situ. In a second instance, and more typically, the term "bioerodible" refers to a pellet composed of an active agent and an excipient composition containing one or more excipients wherein each excipient is (a) a water-soluble and/or bioresorbable compound, or (b) transformed in situ to water-soluble or bioresorbable species, or (c) both (a) and (b), so that all products of pellet bioerosion are dissolved or absorbed within the body, and thus naturally and benignly cleared by the body.

The term "controlled release" refers to a drug-containing formulation or dosage form, e.g., subdermal implant, which does not result in immediate release of the drug into an absorption pool. The term is used interchangeably with "nonimmediate release" as defined in *Remington: The Science and Practice of Pharmacy, Nineteenth Ed.* (Easton, Pa.: Mack Publishing Company, 1995). "Controlled release" for the present purpose includes "sustained release" (synonymous with "extended release"), referring to a formulation that provides for gradual release of an active agent over an extended period of time.

The term "subdermal" to refer to the intended in situ location of the implanted pellet means that the pellet is introduced at an interior body location beneath the skin, where release of the active agent occurs beneath the skin and enters the systemic circulation, i.e., the implantable pellets of the invention provide for "systemic" drug delivery. The subdermally implanted pellets can additionally exhibit a local therapeutic effect, e.g., with respect to tumors, localized inflammation, or the like, by virtue of higher active agent levels present in the vicinity of the pellet. Subdermal implantation includes subcutaneous implantation as well as deeper implantation (the latter generally being the case with hormone replacement therapy, for example, wherein the implant is typically injected into the deeper fatty layers of the stomach or buttocks rather than subcutaneously).

The term "lipophilic" as used herein refers to a pellet or to a pellet segment (e.g., shell or core) containing less than 50 wt. % hydrophilic materials, where "hydrophilic" materials in this context are materials having an aqueous solubility greater than about 50 mg/mL (5 wt. %). It will be appreciated that a pellet, core, or shell that contains 50 wt. % or more of a lipophilic active agent is lipophilic as a result, even if the pellet, core, or shell contains one or more hydrophilic excipients, because the hydrophilic excipients necessarily represent less than 50 wt. % of the pellet.

The term "water soluble" refers to a compound having an aqueous solubility greater than about 30 mg/mL (i.e., 3 wt. %), typically greater than about 50 mg/mL (i.e. 5 wt. %).

A "lipidic material" refers to a composition comprising one or more lipidic compounds that in combination represent greater than 50 wt. % of the lipidic material, wherein "lipidic compounds" include lipids per se, i.e., naturally occurring lipids, whether obtained from a biological source or chemically synthesized in whole or in part; lipid analogs; lipid derivatives; lipid conjugates; and the like.

The term "flowable" refers to a composition that has been transformed, by the application of heat and/or other means (e.g., formation of a suspension, slurry, or the like), from a solid or substantially solid form to a composition that flows. Normally, the transformation is effected thermally, within the context of a hot melt manufacturing process, in which case the flowable composition so provided is also referred to herein as "molten." The approximate temperature at which a pellet, shell, or core composition undergoes this transition is referred to herein as the "transition temperature." The transition temperature may be seen as a melting temperature, although since the compositions herein are usually mixtures, composed of two or more different compounds, there is no definite melting point (unless characterized using an empirical method such as the determination of dropping point or slip point).

The term "substantially homogeneous" indicates a material in the form of a mixture of two or more components in which the material is substantially uniform throughout, with any two discrete regions within the material differing by at most about 20%, preferably by at most about 10%, and most preferably by at most about 5%, with respect to a chemical or physical property of the material, such as the presence or absence of a component, the concentration of a component, the degree of hydrophilicity or lipophilicity, density, crystallinity, or the like.

"Pharmacologically active" (or simply "active"), as in a "pharmacologically active" analog, derivative or other version of an active agent, refers to a compound having the same type of pharmacological activity as the parent compound and approximately equivalent in degree. Therefore, when referring to an active agent, whether specified as a particular compound (e.g., naproxen) or a compound class (e.g., a non-steroidal anti-inflammatory agent), the term used is intended to encompass not only the specified molecular entity or entities but also pharmaceutically acceptable, pharmacologically active analogs and derivatives thereof, including, but not limited to, salts, esters, prodrugs, conjugates, active metabolites, crystalline forms, enantiomers, stereoisomers, and other such derivatives, analogs, and related compounds.

In particular, as an example, when referring to a specific hormone, i.e., a progestogen or an estrogen, it is to be understood that the term not only refers to the agent per se in unmodified form, but also refers to pharmacologically active, pharmaceutically acceptable esters of the agent. For instance, a reference to "hydroxyprogesterone" (17α-hydroxyprogesterone) includes not only hydroxyprogesterone per se but also pharmacologically active, pharmaceutically acceptable hydroxyprogesterone esters such as hydroxyprogesterone caproate, hydroxyprogesterone acetate, and hydroxyprogesterone heptanoate.

It should also be noted that an active agent may be biologically obtained or partially or wholly chemically synthesized.

The terms "effective amount" and "therapeutically effective amount" of an agent, compound, or composition refer to an amount that is nontoxic and effective for the intended purpose.

The term "approximately" in any context is intended to connote a possible variation of at most about 20%. Generally, the term connotes a possible variation of at most about 10%, preferably at most about 5%. The term "substantially" is defined in an analogous manner.

An "excipient" herein refers to any component within the drug delivery system that is an inactive ingredient, such that all components other than the active agent are referred to herein as "excipients." Any excipient used should be "pharmaceutically acceptable," meaning not biologically or otherwise undesirable, so that that the excipient can be incorporated into a dosage form administered to a patient without causing any significant undesirable biological effects or interacting in a deleterious manner with any other components of the dosage form. "Pharmaceutically acceptable" excipients herein meet the criteria set out in the Inactive Ingredient prepared by the U.S. Food and Drug Administration, and, preferably, have also been designated "Generally Regarded as Safe" ("GRAS").

By "long-term" administration is meant delivery of a drug to a subject throughout an extended drug delivery time period, on the order of about three months to about four years or more. "Chronic" drug administration refers to long-term administration that typically involves treatment of a chronic condition likely to persist in the absence of treatment, or prevention of a chronic condition likely to occur or reoccur in the absence of drug administration.

The terms "treating" and "treatment" as used herein refer to reduction in severity and/or frequency of symptoms, elimination of symptoms and/or underlying cause, and improvement or remediation of damage. Unless otherwise indicated, the terms "treating" and "treatment" as used herein encompass prevention of symptoms as well.

As used herein, the terms "subject," "individual," and "patient" refer to any individual, including humans and non-human mammals, for whom the present drug delivery system is intended and to whom an active agent is administered as described herein. The subject may be human or a non-human animal, generally a mammal. Veterinary use of the present drug delivery system is thus envisioned.

II. Pellet Composition:

The drug delivery system of the invention is composed of at least one subdermally implantable, bioerodible pellet that provides for controlled, sustained release of an active agent contained therein during an extended drug delivery time period. A pellet may contain a single active agent or two or more active agents, and with drug delivery systems composed of two or more pellets, all pellets may contain the same active agent or different active agents may be incorporated into different pellets.

The invention is not limited with respect to particular active agents or active agent classes. For practical purposes, however, it is generally preferred that the active agent selected for incorporation into an implantable pellet is solid at temperatures below about 40° C. Active agents should also have an aqueous solubility below about 50 mg/mL, more preferably below about 30 mg/mL. In addition, potent active agents, i.e., active agents that are effective at relatively low dosages, are preferred, insofar as a lower quantity of active agent per pellet is necessary. This in turn minimizes the number and/or size of pellets needed to provide therapeutic efficacy over the effective drug delivery time period. "Potent" active agents in the present context are generally drugs that are effective at a daily dosage of less than about 10 mg, preferably less than 5 mg, and more preferably less than 1 mg. Optimally, potent active agents herein are therapeutically effective at a dose in the range of about 0.1 mg/day to about 0.5 mg/day.

In general, the active agent(s) herein may be selected from any of the generally recognized classes of pharmacologically active agents, including, without limitation: analgesic agents; anti-anxiety agents; anti-arthritic agents; anti-asthmatic agents; anticancer agents; anticholinergic agents; anticholinesterases; anticonvulsants; antidepressants; antidiabetic agents; antidiarrheal agents; anti-emetic agents; antihistamines; antihyperlipidemic agents; anti-infective agents; anti-inflammatory agents; antimigraine agents; anti-obesity agents; agents; antipruritic agents; antipsychotic agents; antispasmodic agents; agents for treating neurodegenerative diseases; cardiovascular medicaments; diuretic agents; gastrointestinal medicaments; hormones and antihormones; hypnotic agents; immunosuppressive agents; leukotriene inhibitors; narcotic agonists and antagonists; neurotransmitters; nicotine; nucleic acids; peptide drugs; phytonutrients; sympathomimetic agents; thrombolytic agents; vasodilators; vitamins and mineral supplement; and combinations thereof.

Examples of preferred subclasses and specific agents therein include, without limitation, the following:

Analgesic agents, which include opioid analgesics such as alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol; and nonopioid analgesics such as apazone, etodolac, diphenpyramide, indomethacin, meclofenamate, mefenamic acid, oxaprozin, phenylbutazone, piroxicam, and tolmetin.

Anti-anxiety agents ("anxiolytics"), which include benzodiazepines such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; buspirone, and droperidol.

Anticancer agents, including any type of active agent that acts to eliminate, mitigate, or otherwise treat cancer. Anticancer agents that are generally referred to as chemotherapy agents include antimetabolites, e.g., anti-folates such as methotrexate and pemetrexed; fluoropyrimidines such as fluorouracil and capecitabine; deoxynucleoside analogs such as cytarabine, gemcitabine, decitabine azacitidine, fludarabine, nelarabine, cladribine, clofarabine, and pentostatin; and thiopurines such as thioguanine and mercaptopurine. Other types of chemotherapy agents are anti-microtubule agents such as paclitaxel, docetaxel, vindesine, and vinflunine; topoisomerase inhibitors such as irinotecan, topotecan, etoposide, and teniposide; and cytotoxic antibiotics such as aclararubicin, pirarubicin, mitoxantrone, mitomycin.

Another subclass of anticancer agents is used to provide any of several types of hormonal therapy, where the active agents are inhibitors of hormone synthesis, hormone receptor antagonists, or hormone supplements. Hormone synthesis inhibitors include aromatase inhibitors such as letrozole, anastrozole, exemestane, megestrol acetate, aminoglutethimide, typically used to treat breast cancer; and analogs of gonadotropin-releasing hormone (GnRH), such as leuprorelin, goserelin, and histrelin, used in the treatment of prostate cancer. Hormone receptor antagonists include selective estrogen receptor modulators (SERMS) such as tamoxifen, raloxifene, toremifene, and fulvestrant, as well as anti-androgens such as flutamide and bicalutamide.

Additional anticancer agents of use herein also include anti-angiogenic agents, such bevacizumab, itraconazole, ranibuzamab, ramucirumab, prolactin, and other VEGF inhibitors; cell proliferation inhibitors such as angiostatin, endostatin, and thrombospondin; and exogenous matrix metalloproteinase inhibitors, such as batimastat, cipemastat, ilomastat, marimastat, MMI270, prinomastat, rebimastat, and tanomastat.

Another class of anticancer agents of use in conjunction with the invention are hormone supplements, such as megestrol acetate, medroxyprogesterone, fluoxymesterone, and octreotide.

Anticholinergic agents, i.e., acetylcholine blockers useful in the treatment of a number of conditions. Representative anticholinergic agents include, without limitation, atropine, scopolamine, glycopyrrolate, trihexyphenidyl, biperiden, metixene, procyclidine, profenamine, dexetimide, phenglutarimide, mazaticol, bornaprine, and tropatepine.

Anticonvulsant agents, including anti-epileptic agents, with representative examples of such agents including aminobutyric acid, acetazolamide, carbamazepine, clonazepam, clorazepate, ethadione, ethosuximide, ethotoin, felbamate, foxphenytoin, gabapentin, lamotrigine, levetiracetam, mephenytoin, methylphenobarbital, oxycarbazepine, phenytoin, pheneturide, phenobarbital, phensuximide, pregabalin, primidone, progabide, rufinamide, tiagabine, topiramate, trimethadione, valproic acid, valpromide, vigabatrin, and zonisamide.

Antidepressants, including (a) tricyclic antidepressants such as amoxapine, amitriptyline, clomipramine, desipramine, doxepin, imipramine, maprotiline, nortryptiline, protryptiline, and trimipramine, (b) serotonin reuptake inhibitors such as citalopram, escitalopram, fluoxetine, fluvoxamine, paroxetine, sertraline, and venlafaxine, (c) monoamine oxidase inhibitors such as phenelzine, tranylcypromine, and (-)-selegiline, and (d) other, "atypical" antidepressants such as bupropion, nefazodone, trazodone, and venlafaxine.

Antiemetic agents, including, without limitation, chlorpromazine, cisapride, domperidone, granisetron, metoclopramide, ondansetron, perphenazine, prochlorperazine, promethazine, thiethylperazine, and triflupromazine;

Antihistamines administrable in conjunction with the delivery systems of the invention include, without limitation, H1 antihistamines such as the H1 antagonists diphenhydramine, cetirizine, chlorpheniramine, dimenhydrinate, diphenhydramine, fexofenadine, hydroxyzine, orphenadrine, pheniramine, and doxylamine; and H2 antihistamines, including cimetidine, famotidine, lafutidine, nizatidine, ranitidine, and roxatidine.

Antihyperlipidemic agents, which include the HMG CoA reductase inhibitors lovastatin, simvastatin, atorvastatin, pravastatin, fluindostatin, mevastatin, velostatin, and cerivastatin; bile acid sequestrants such as cholestyramine, cholestipol, colesevalam; and fibric acid derivatives such as bezafibrate, beclobrate, binifibrate, ciprofibrate, clinofibrate, clofibrate, etofibrate, fenofibrate, gemfibrozil, nicofibrate, pirifibrate, ronifibrate, simfibrate, and theofibrate.

Anti-inflammatory agents, used to treat numerous indications, include both non-steroidal anti-inflammatory agents and steroidal anti-inflammatory agents. NSAIDS include propionic acid derivatives such as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen and tiaprofenic acid; acetylsalicylic acid; apazone; diclofenac; difenpiramide; diflunisal; etodolac; flufenamic acid; indomethacin; ketorolac; meclofenamate; mefenamic acid; nabumetone; phenylbutazone; piroxicam; salicylic acid; sulindac; tolmetin; oxicams such as meloxicam and piroxicam; nabumetone; phenylbutazone; piroxicam; salicylates such as salsalate and acetylsalicylic acid; sulfasalazine; sulindac; tolmetin; and COX-2 inhibitors such as celecoxib, rofecoxib, and valdecoxib.

Steroidal anti-inflammatory agents include corticosteroids of varying potency. Representative corticosteroids of lower to moderate potency include hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, and methylprednisolone. Higher potency corticosteroids, which are generally preferred herein for reasons discussed above, include drugs such as betamethasone, typically as betamethasone benzoate or betamethasone diproprionate; fluocinonide; prednisone; and triamcinolone, typically as triamcinolone acetonide.

Anti-infective agents: the drug delivery system and method of the invention can be used to provide long-term sustained release of a variety of anti-infective agents, including antibiotics, antiviral agents; antifungal agents; and antiparasitic agents.

Suitable antibiotic agents include, without limitation, (a) tetracycline antibiotics and related compounds, such as chlortetracycline, oxytetracycline, demeclocycline, methacycline, doxycycline, and rolitetracycline;

(b) macrolide antibiotics such as erythromycin, clarithromycin, and azithromycin;

(c) streptogramin antibiotics such as quinupristin and dalfopristin;

(d) beta-lactam antibiotics, including penicillins (e.g., penicillin G, penicillin VK), antistaphylococcal penicillins (e.g., cloxacillin, dicloxacillin, nafcillin, and oxacillin), extended spectrum penicillins (e.g., aminopenicillins such as ampicillin and amoxicillin, and the antipseudomonal penicillins such as carbenicillin), cephalosporins (e.g., cefadroxil, cefepime, cephalexin, cefazolin, cefoxitin, cefotetan, cefuroxime, cefotaxime, ceftazidime, and ceftriazone), and carbapenems such as imiprenem, meropenem and aztreonam;

(e) aminoglycoside antibiotics such as streptomycin, gentamicin, tobramycin, amikacin, and neomycin;

(f) glycopeptide antibiotics such as vancomycin and teicoplanin;

(g) sulfonamide antibiotics such as sulfacetamide, sulfabenzamide, sulfadiazine, sulfadoxine, sulfamerazine, sulfamethazine, sulfamethizole, and sulfamethoxazole;

(h) quinolone antibiotics such as ciprofloxacin, nalidixic acid, and ofloxacin;

(i) anti-mycobacterials such as isoniazid, rifampin, rifabutin, ethambutol, pyrazinamide, ethionamide, aminosalicylic, and cycloserine; and (j) miscellaneous antibacterial agents such as chloramphenicol, spectinomycin, polymycin B (colistin), and bacitracin.

Antiviral agents, including antiretroviral agents, can also be delivered using the present systems. Representative antiviral agents include, without limitation, acyclovir, famcyclovir, ganciclovir, foscarnet, idoxuridine, sorivudine, trifluorothymidine, valacyclovir, vidarabine, didanosine, dideoxyinosine, stavudine, zalcitabine, zidovudine, amantadine, interferon alpha, ribavirin and rimantadine.

Systemic antifungal agents suitable for delivery using the present system include, without limitation, itraconazole, ketoconazole, fluconazole, and amphotericin B. Examples of antiparasitic agents suitable herein include the broad spectrum antiparasitic medicament nitazoxanide; antimalarial drugs and other antiprotozoal agents (e.g., artemisins, mefloquine, lumefantrine, tinidazole, and miltefosine); anthelminthics such as mebendazole, thiabendazole, and ivermectin; and antiamoebic agents such as rifampin and amphotericin B.

Antipsychotic drugs that can be administered herein. Antipsychotic drug delivery is a significant application of the present invention, insofar as patient compliance is commonly problematic, often with dire consequences. Examples of antipsychotic drugs that can be administered using the present system include (a) phenothiazines such as acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, pipothiazine, pipothiazine palmitate, thioridazine, thioridazine hydrochloride, trifluoperazine, and trifluoperazine hydrochloride; (b) thioxanthenes such as chlorprothixene, flupenthixol, flupenthixol decanoate, thiothixene, thiothixene hydrochloride, and zuclopenthixol; (c) other heterocyclic drugs such as aripiprazole, carbamazepine, clozapine, droperidol, haloperidol, haloperidol decanoate, iloperidol, lamotrigine, loxapine succinate, molindone, molindone hydrochloride, olanzapine, pimozide, quetiapine, paliperodone; risperidone, and sertindole; and (d) other antipsychotic agents such as lithium, valproic acid, and valproic acid esters, salts, and other derivatives.

Preferred antipsychotic agents for long-term administration using the present controlled release systems include haloperidol, haloperidol decanoate, iloperidone, flupenthixol, flupenthixol decanoate, paliperodone, olanzapine, aripiprazole, pipoxanthine, zuclopenthixol (preferably as the decanoate, acetate, or dihydrochloride), lithium, risperidone, valproic acid, sodium valproate, and lamotrigine, with haloperidol and risperidone representing exemplary antipsychotic agents herein, in terms of both potency and thermal stability.

As with antipsychotic agents, compliance can be a serious problem with patients taking medication for treatment of a neurodegenerative disorder such as Alzheimer's disease, Huntington's disease, Parkinson's disease, and amyotrophic lateral sclerosis. Active agents for treating Alzheimer's disease and Huntington's disease are useful for treating dementias and/or enhancing memory and learning processes, and include, for instance, donezepil, donepezil hydrochloride, physostigmine, physostigmine salicylate, tacrine and tacrine hydrochloride, while fluoxetine and carbamazepine are used to treat Huntington's Disease. Anti-Parkinsonism drugs useful herein include amantadine, apomorphine, bromocriptine, levodopa (particularly a levodopa/carbidopa combination), pergolide, ropinirole, selegiline, trihexyphenidyl, and trihexyphenidyl hydrochloride, and anticholinergic.

Cardiovascular medicaments administrable in conjunction with the invention include antiarrhythmic agents, antihypertensive agents, and anti-anginal agents, with antiarrhythmic agents including digoxin and beta-blockers such as timolol, atenolol, and betaxolol, and the primary antianginal agent being nitroglycerin. Antihypertensive agents include, without limitation: angiotensin-converting-enzyme (ACE) inhibitors such as captopril, zofenopril, fosinopril, enalapril, lisinopril, benazepril, and imidapril; dihydropyridine (DHP) calcium channel blockers such as amlodipine, dihydropyridine, felodipine, nifedipine, nicardipine, nimodipine, and nisoldipine; phenylalkylamine calcium channel blockers such as fendiline, gallopamil, and verapamil; benzothiazepine calcium channel blockers such as diltiazem; and angiotensin II receptor antagonists such as valsartan, losartan, irbesartan, and olmesartan; alpha blockers such as doxazosin, indoramine, phenoxybenzamine, phentolamine, prazosin, tolazoline, terazosin, trimazosin, tamsulosin, and yohimbine; and other antihypertensive agents including clonidine, apraclonidine, guanfacine, and guanabenz.

In addition to the corticosteroids identified above as anti-inflammatory agents, other types of steroid hormones can also be advantageously administered with the present drug delivery system. Examples include progestogens such as 21-acetoxypregnenolone, allylestrenol, anagestone 17α-hydroxy-6α-methylpregn-4-en-20-one, anagestone 17α-acetate, chlormadinone, chlormadinone 17α-acetate, chloroethynyl norgestrel, cyproterone, cyproterone 17α-acetate, desogestrel, dienogest, dimethisterone (6α,21-dimethylethisterone), drospirenone (1,2-dihydrospirorenone), ethisterone (17α-ethinyltestosterone or pregneninolone), ethynerone, etynodiol diacetate (norethindrol diacetate), etonogestrel (11-methylene-levo-norgestrel; 3-keto-desogestrel), gestodene, hydroxyprogesterone (17α-hydroxyprogesterone), hydroxyprogesterone caproate, hydroxyprogesterone acetate, hydroxyprogesterone heptanoate, levonorgestrel, lynestrenol, medrogestone (6,17α-dimethyl-6-dehydroprogesterone), medroxyprogesterone, medroxyprogesterone acetate, megestrol, megestrol acetate, segesterone acetate, nomegestrol, nomegestrol acetate, norethindrone (norethisterone; 19-nor-17α-ethynyltestosterone), norelgestromin (17-deacetylnorgestimate), noretynodrel, norgestrienone, progesterone, and retroprogesterone. Progestogens within this group that are sometimes preferred include, by way of example only, desogestrel, dienogest, drospirenone, ethisterone, etonogestrel, gestodene, levonorgestrel, medroxyprogesterone, megestrol, norethindrone, norgestimate, and esters of any of the foregoing, when the compound allows for esterification (e.g., medroxyprogesterone acetate, megestrol acetate, and norethindrone acetate). Within this group, the progestogenic agents that are generally preferred include etonogestrel and levonorgestrel.

Another example of a type of steroid that can be administered with the systems of the invention is an estrogen, i.e., an estrogenic compound. Estrogenic compounds include synthetic and natural estrogens such as: estradiol (i.e., 1,3,5-estratriene-3,17β-diol, or "17β-estradiol") and its esters, including estradiol benzoate, valerate, cypionate, heptanoate, decanoate, acetate and diacetate; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Generally preferred such compounds include 17β-estradiol, estetrol, estriol, estrone, ethinyl estradiol, mestranol, moxestrol, quinestrol, conjugated estrogens, and combinations thereof.

A steroid combination can also be included in the implantable pellets, for example to provide a sustained release male contraceptive system. Typically, although not necessarily, the steroid combination in this context includes a progestogen, such as a progestogen identified above, and an androgenic agent. Suitable androgenic agents for incorporation into a male contraceptive system herein include, but are not limited to: naturally occurring androgens and derivatives thereof including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone (DHT; also termed "stanolone"), 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone. The weight ratio of the progestogen to the androgen will typically be in the range of about 1:5 to about 5:1, more typically in the range of about 1:3 to about 3:1.

Peptide drugs, including amino acids, oligopeptides, polypeptides, and proteins, can also be delivered with the present systems. Such drugs include coagulation modulators, cytokines, endorphins, peptidic hormones, leuteinizing hormone-releasing hormone (LHRH) analogues, kinins, and enzyme inhibitors, with specific examples as follows:

Coagulation modulators, such as α1-antitrypsin, α2-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, thrombomodulin and combinations thereof;

Cytokines, such as transforming growth factors (TGFs), including TGF-β1, TGF-β2, and TGF-β3; bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), heparin-binding neurotrophic factor (HBNF), and insulin-like growth factor (IGF)); connective tissue activated peptides (CTAPs), osteogenic factors; colony stimulating factor; interferons, including interferon-α, interferon α-2a, interferon α-2b, interferon α-n3, interferon-beta, and interferon-γ; interleukins, including interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, and interleukin-17; tumor necrosis factor; tumor necrosis factor-alpha; granulocyte colony-stimulating factor (G-CSF); granulocyte-macrophage colony-stimulating factor (GM-CSF); macrophage colony-stimulating factor; inhibins (e.g., inhibin A and inhibin B); growth differentiating factors (e.g., GDF-1); activins (e.g., activin A, activin B, and activin AB); midkine (MD); and thymopoietin;

Endorphins, i.e., peptides that activate opiate receptors, including pharmacologically active endorphin derivatives such as dermorphin, dynorphin, α-endorphin, β-endorphin, γ-endorphin, σ-endorphin [Leu5]enkephalin, [Met5]enkephalin, substance P, and combinations thereof;

Peptidic hormones, such as activin, amylin, angiotensin, atrial natriuretic peptide (ANP), calcitonin (derived from chicken, eel, human, pig, rat, salmon, etc.), calcitonin gene-related peptide, calcitonin N-terminal flanking peptide, cholecystokinin (CCK), ciliary neurotrophic factor (CNTF), corticotropin (adrenocorticotropin hormone, ACTH), corticotropin-releasing factor (CRF or CRH), follicle-stimulating hormone (FSH), gastrin, gastrin inhibitory peptide (GIP), gastrin-releasing peptide, glucagon, gonadotropin-releasing factor (GnRF or GnRH), growth hormone releasing factor (GRF, GRH), human chorionic gonadotropin (hCG), inhibin A, inhibin B, insulin (derived from beef, human, pig, etc.), leptin, lipotropin (LPH), luteinizing hormone (LH), luteinizing hormone-releasing hormone (LHRH), lypressin, α-melanocyte-stimulating hormone, β-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatostatin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, triiodothyronine, vasoactive intestinal peptide (VIP), and vasopressin (antidiuretic hormone, ADH);

Analogues of LHRH, such as buserelin, deslorelin, fertirelin, goserelin, histrelin, leuprolide (leuprorelin), lutrelin, nafarelin, tryptorelin and combinations thereof;

Kinins, such as bradykinin, potentiator B, bradykinin potentiator C, and kallidin and combinations thereof; and Enzyme inhibitors, such as leupeptin, chymostatin, pepstatin, renin inhibitors, and the like.

In addition to peptide drugs, other types of biomolecules can also be administered with the present systems, particularly nucleic acids, including gene fragments, oligonucleotides and polynucleotides, antisense oligonucleotides and polynucleotides, oligonucleotides and polynucleotides containing one or more nonnatural amino acids and/or nonnatural internucleotide linkage, or any other nucleic acid having biological activity or other benefit. Other biomolecules of interest herein include lipids, lipoproteins, lipopolysaccharides, polysaccharides, and the like.

Other examples of active agents and active agent subclasses that are useful in conjunction with the present invention include, without limitation, the following:

anti-diarrheal agents such as loperamide and cholestyramine;

muscle relaxants (antispasmodic agents) such as methocarbamol, carisoprodol, cyclobenzaprine, metaxalone, mebeverine, papaverine;

anti-ulcer and other gastrointestinal drugs such as ranitidine and the proton pump inhibitors omeprazole, dexlansoprazole, lansoprazole, and esomeprazole;

appetite suppressants such as dextroamphetamine, diethylpropion, mazindol, and phentermine;

hypnotics and sedatives, such as clomethiazole, ethinamate, etomidate, glutethimide, meprobamate, methyprylon, zolpidem, and barbiturates (e.g., amobarbital, apropbarbital, butabarbital, butalbital, mephobarbital, methohexital, pentobarbital, phenobarbital, secobarbital, thiopental);

synthetic hormones such as levothyroxine;

sympathomimetic agents, i.e., central nervous system stimulants, such as agents for treating attention deficit disorder (ADD) and attention deficit hyperactivity disorder;

neurotransmitters, such as GABA (γ-aminobutyric acid), glycine, acetylcholine, dopamine, epinephrine, 5-hydroxytryptamine, serotonin, enkaphalins and related opioid peptides as above, and catecholamines;

narcotic agonists and antagonists such as naloxone, naltrexone, nalorphine, nalmefene, levalorphan; and other agents for treating addiction disorders, such as disulfiram, nicotine, bupropion, varenicline, disulfiram, calcium carbimide, acamprosate, buprenorphine, methadone, levacetylmethadol, lofexidine, betahistine, cinnarizine, flunarizine, acetylleucine, gangliosides and ganglioside derivatives, tirilazad, riluzole, xaliproden, hydroxybutyric acid, and amifampridine.

In addition to pharmacologically active agents typically thought of as pharmaceuticals, other types of active agents referred to herein as "nutrients" can also be administered using the present delivery systems. Nutrients include vitamin, mineral and nutritional supplements, and the like.

Vitamins, minerals, and other nutritional supplements are naturally present as trace organic substances that are required in the diet, and include, without limitation, thiamin, riboflavin, nicotinic acid, pantothenic acid, pyridoxine, biotin, folate, vitamin $B_{12}$, vitamin A, vitamin D, vitamin E and vitamin K. Also included within the term "vitamin" are the coenzymes thereof, such as thiamine pyrophosphates (TPP), flavin mononucleotide (FMM), flavin adenine dinucleotide (FAD), nicotinamide adenine dinucleotide (NAD), nicotinamide adenine dinucleotide phosphate (NADP), Coenzyme A (CoA), Coenzyme Q (CoQ), pyridoxal phosphate, biocytin, tetrahydrofolic acid, and coenzyme $B_{12}$. The term "vitamin" also includes choline and carnitine. The term "mineral" refers to inorganic substances that are required in the human diet, and includes, without limitation, calcium, magnesium, iron, zinc, selenium, copper, manganese, chromium, molybdenum, etc. Other nutritional supplements include amino acids, terpenoids, curcumin, resveratrol, lignans, carnitine, carnosine, carotene, choline, chondroitin sulfate, coenzyme Q10, creatine, dehydroepiandrosterone, 5-hydroxytryptophan, indole-3-carbinol, methyl sulfonylmethane, phospholipids, phytosterols, essential fatty acids (e.g., omega-3 fatty acids), green tea polyphenols, quercetin and other flavonoids, S-adenosylmethionine, theobromine, and tocotrienols, among others. Further examples of suitable nutrients include those listed in Handbook of Nutraceuticals and Functional Foods, Robert E. C. Wildman, Ed., CRC Press (2001).

The amount of the pharmacologically active agent in a drug delivery system of the invention comprising a subdermally implantable pellet is selected to result in serum levels of the agent sufficient to provide therapeutic efficacy during the effective drug delivery time period, taking the release rate, length of the intended drug delivery time period, and specific active agent into account. Another consideration is whether the intended therapeutic effect includes a local therapeutic effect. That is, when the system is implanted in the region of an individual tumor, an isolated site of inflammation, or the like, the intention is to provide higher levels of active agent in the vicinity of the implant, which in turn impacts on the amount of active agent to be incorporated into a pellet. It should be noted that although the drug delivery system may be composed of only one subdermally implantable pellet, it may also be composed of multiple pellets, e.g., two to six pellets, such as four or five pellets. When the drug delivery system is composed of more than one pellet, the number of pellets implanted is also taken into account in determining the amount of active agent to incorporate into a single pellet. The optimum amount is preferably calculated for a drug delivery time period in the range of about three months to about four years, e.g., in the range of about six months to about four years; in the range of about six months to about three years; and in the range of about one year to about three years, for instance about 18 months.

Drug loading may be in the range of about 20 wt. % to about 100 wt. %., preferably in the range of about 50 wt. % to about 99 wt. %, more preferably in the range of about 75 wt. % to about 95 wt. %. The aforementioned ranges pertain to the percentage of an active agent in a monolithic pellet, or, for a core-type pellet or a shell-type pellet, the percentage of the active agent in the shell or core, respectively. Optimal drug loading may approximate 85 wt. %. The degree of drug loading can be altered to vary drug release profile as desired. As shown in Example 7, increasing the fraction of active agent in the pellet generally results in an increase in drug release rate.

The pellets may be wholly composed of active agent, but generally, and preferably, contain an excipient composition as well, where the excipient composition may be a single excipient or it may include two or more excipients. Excipients for incorporation into the present pellets along with the active agent should be selected so as to avoid compromising the bioerodibility of the pellet as a whole. This means that any excipients should be bioresorbable, water soluble, or both, and/or degrade or otherwise transform in vivo, during bioerosion of the pellet, to bioresorbable and/or water-soluble species. Preferred excipients are naturally occurring compounds, which may be obtained from a biological source or chemically synthesized in whole or in part. One or more excipients may be hydrophilic, providing that the pellet as a whole is still lipophilic. For core-type pellets and shell-type pellets, both the core and the shell should be lipophilic, meaning that the core and shell each contain less than 50 wt. % hydrophilic materials, preferably less than 45 wt %, less than 40 wt. %, less than 35 wt. %, less than 30 wt. %, less than 25 wt. %, less than 20 wt. %, less than 15 wt. %, less than 10 wt. %, or less than 5 wt. % of the pellet. "Hydrophilic" materials, as noted previously, are materials having an aqueous solubility of at least about 3 wt. %, e.g., at least about 5 wt. %, or the like. For example, a pellet, core, or shell that contains a lipophilic active agent, with the lipophilic active agent representing at least 50 wt. % of the pellet, core, or shell, respectively, is necessarily lipophilic, insofar as the total hydrophilic components represent less than 50 wt. % of the pellet, core, or shell composition.

Excipients may or may not be solid at body temperature and under storage conditions, so long as: (1) the pellet as a whole is substantially solid at body temperature and during storage, i.e., at temperatures in the range of about 35° C. to about 40° C.; and (2) the pellet composition is flowable at a selected temperature in the range of about 50° C. to about 250° C., particularly when a hot melt manufacturing technique—such as the manufacturing process described herein—is used. In addition, excipients should be selected so that the pellet does not fracture or break during or after implantation. This may require inclusion of a softening agent as an excipient, e.g., lecithin. However, the pellet should still be hard enough so that it can be palpated after implantation, to confirm or determine location.

Suitable excipients include, but are not limited to, lipidic compounds, e.g., lipids per se, including naturally occurring lipids and lipids that are chemically synthesized in whole or in part; lipid analogs; lipid derivatives; lipid conjugates; and the like. Naturally occurring lipids and readily hydrolyzable esters of naturally occurring lipids are generally preferred lipidic excipients, insofar as such compounds facilitate bioabsorption and bioerosion to nontoxic molecular components. For example, a lipidic excipient may be a sterol, a sterol ester, or a combination thereof, including, without limitation, cholesterol, 7-dehydrocholesterol, cholestatrienol, cholestanol, cholesteryl acetate, desmosterol, dehydroergosterol, thiocholesterol, 3-keto-delta-5-cholestene, 7-methylenecholesterol, epicholesterol, lathosterol, lanosterol, dihydrocholesterol, 25-hydroxycholesterol, cholestane, cholestane diol, cholest-4-en-3-one, and zymosterol. In some embodiments, cholesterol is a preferred lipidic excipient herein.

Other lipidic compounds that can serve as excipients herein include, but are not limited to, the following: phospholipids such as phosphorylated diacyl glycerides, particularly phospholipids selected from the group consisting of diacyl phosphatidylcholines, diacyl phosphatidylethanolamines, diacyl phosphatidylserines, diacyl phosphatidylinositols, diacyl phosphatidylglycerols, diacyl phosphatidic acids, and mixtures thereof, wherein each acyl group contains about 10 to about 22 carbon atoms and is saturated or unsaturated; fatty acids such as isovaleric acid, valeric acid, caproic acid, enanthic acid, caprylic acid, pelargonic acid, capric acid, lauric acid, myristic acid, palmitic acid, stearic acid, arachidic acid, behenic acid, lignoceric acid, oleic acid, linoleic acid, linolenic acid, and arachidonic acid; lower fatty acid esters comprising esters of the foregoing fatty acids, wherein the carboxylic acid group of the fatty acid is replaced with an ester moiety —(CO)—OR wherein R is a $C_1$-$C_3$ alkyl moiety optionally substituted with one or two hydroxyl groups; fatty alcohols corresponding to the aforementioned fatty acids, wherein the carboxylic acid group of the fatty acid is replaced by a —$CH_2OH$ group; glycolipids such as cerebroside and gangliosides; oils, including animal oils such as cod liver oil and menhaden oil, and vegetable oils such as babassu oil, castor oil, corn oil, cottonseed oil, linseed oil, mustard oil, olive oil, palm oil, palm kernel oil, peanut oil, poppyseed oil, rapeseed oil, safflower oil, sesame oil, soybean oil, sunflower seed oil, tung oil, or wheat germ oil; and waxes, i.e., higher fatty acid esters, including animal waxes such as beeswax and shellac, mineral waxes such as montan, petroleum waxes such as microcrystalline wax and paraffin, and vegetable waxes such as carnauba wax.

A lipidic excipient may also be incorporated into the pellets in a combination or mixture of two or more excipients (including mixtures of two or more lipidic excipients), for example having different aqueous solubilities and/or with one of the excipients selected to serve a particular purpose (e.g., functioning as a softening agent). For example, a pellet may contain a combination of a lipidic excipient having a first aqueous solubility and a second excipient, which may or may not be lipidic, having a second aqueous solubility, where the first aqueous solubility is lower than the second aqueous solubility by at least 5%, typically by at least 10%. The weight ratio of the less soluble excipient to the more soluble excipient may be in the range of about 2:1 to about 100:1, more typically in the range of about 3:1 to about 50:1, and optimally about 3.5:1 to about 25:1, e.g., 4:1. The examples herein describe such excipient compositions, wherein cholesterol serves as the lipidic excipient with a first aqueous solubility and lecithin or a component thereof (e.g., phosphatidylcholine) serves as the second excipient.

Additional excipients that can be incorporated into the pellets instead of, or in addition to, a lipidic excipient as described above, include, without limitation, phospholipids and phospholipid mixtures, e.g., lecithin (a phospholipid mixture) and glycerophospholipids such as phosphatidylcholine, phosphatidylethanolamine, phosphatidylinositol, and phosphatidylserine; polyethylene glycols (PEGs) of different molecular weights, e.g., PEG-300, PEG-1000, PEG-4000, PEG-6000, and PEG-8000; PEG fatty acid esters such as PEG laurates, oleates, stearates, and the like; other gradually erodible synthetic polymers such as polylactides, polyglycolides, polycaprolactones, polyanhydrides, polyurethanes, polyesteramides, polyorthoesters, polyvinylpyrrolidone, and polyhydroxycellulose; polymers typically used to prepare hydrogels, e.g., polyvinyl alcohol, poly(hydroxyethyl methacrylate), and polyacrylic acid; glycerine and glycerinated gelatin; chitin and chitosan; and lower molecular weight excipients such as propylene glycol.

If desired, a radio-opaque material can be incorporated into the present drug delivery systems in order to enable X-ray visualization of the implanted pellets. Suitable radio-opaque materials for this purpose are known in the art and include, for instance, barium sulfate, titanium oxide, bismuth oxide, tungsten, and iodinated contrast agents (i.e., contrast agents based on the 2,4,6-triiodobenzene structure), with barium sulfate more commonly used. Any such radio-opaque material will generally represent in the range of about 2.5 wt. % to about 30 wt. % of a pellet, more typically about 2.5 wt. % to about 15 wt. % of a pellet.

III. Physical and Pharmacokinetic Attributes of the Pellet:

The pellets herein can be of any size, shape or structure that allow for ease of manufacture and implantation, and that contribute to or at least do not detract from the desired pharmacokinetic properties. Generally, for ease of manufacture and implantation, the pellets are rod-shaped, i.e., approximately cylindrical, with length, width, surface area, etc., selected to provide specific pharmacokinetic or other properties, such as drug release rate, drug release profile (i.e., the change in release rate over time), length of the effective drug delivery period, length of any tail period, and the like.

An elongated pellet of the invention may be substantially cylindrical. Such pellets will generally have a length in the range of about 2.0 mm to about 12.0 mm, and a diameter in the range of about 1.0 mm to about 3.5 mm. Typically, pellet length is in the range of about 3.5 mm to about 7.0 mm, with pellet diameter in the range of about 1.0 to about 3.2. In a preferred embodiment, the pellet length is in the range of about 4.0 mm to about 6.5 mm and the pellet diameter is in the range of about 1.3 mm to about 3.0 mm. Exemplary pellet dimensions thus include: diameter 2.8 mm, length 6.0 mm; diameter 2.8 mm, length 4.5 mm; diameter 2.8 mm, length 4.0 mm; diameter 1.7 mm, length 4.0 mm. Additional examples are given below.

In one embodiment, the pellet is monolithic, such that the pellet is comprised of a substantially homogeneous matrix with the pharmacologically active agent is dispersed therein, where "substantially homogeneous" is defined in Part (I) of this section. In such a case, the pellet may be essentially amorphous, or it may be crystalline or partially crystalline, preferably without any interior voids. To check a monolithic pellet for substantial homogeneity, the pellet can be divided into several, e.g., three to six, subsections, and each subsection weighed and dissolved in a known amount of solvent. Each dissolved subsection can then be analyzed using a standard technique, e.g., HPLC, and the relative quantities of components determined and compared to the results in the other subsections.

A standard monolithic pellet will have dimensions as described above.

Monolithic pellets generally have a density in the range of about 0.75 g/cm$^3$ to about 1.25 g/cm$^3$, as do pellets composed of two or more discrete regions, e.g., cores and shells in core-type and shell-type pellets herein. More typically, monolithic pellets typically have a density in the range of about 0.90 g/cm$^3$ to about 1.10 g/cm$^3$, and most typically in the range of about 0.95 g/cm$^3$ to about 1.05 g/cm$^3$.

In another embodiment, the pellet is composed of two or more discrete regions each having a different composition. That is, compositions in different regions may differ with respect to components of the composition, component amount, component concentration, or the like. For example, the pellet may be composed of a first region containing the pharmacologically active agent and a second region containing only inactive ingredients, i.e., excipients. As another example, the first and second region may contain the same pharmacologically active agent, but in different amounts and/or present at different concentrations. Discrete regions may also contain different active agents.

A preferred pellet structure composed of two or more discrete regions is a core-and-shell type of dosage form, where the first region is an inner core and the second region is a shell that partially or entirely encloses the core. With an elongated dosage form such as a cylindrical pellet, the first region may be an inner core having a length, a surface along the length, a first end, and a second end, and the second region may be an outer shell enclosing the surface of the inner core along its length but not the first end or the second end, such that the core has exposed surface area at the first and second ends. This type of structure may be one wherein: at least about 80 wt. % (e.g., at least about 90 wt. %, such as 100%) of the active agent in the pellet is in the core (referred to herein as a "core-type" pellet); at least about 80 wt. % (e.g., at least about 90 wt. %, such as 100%) in the pellet is in the shell (a "shell-type" pellet); or active is present in both the core and the shell with greater 20 wt. % of the active present in each region. In one embodiment, a core-type pellet is composed of an inactive shell with 100% of the active in the core. In another embodiment, a shell-type pellet is composed of an inactive core with 100% of the active in the shell.

Typical dimensions for core-shell structures, including core diameter and shell thickness, are as follows: core diameter, about 1.0 mm to about 2.0 mm, shell thickness about 0.3 mm to about 1.0 mm, and length about 4 mm to about 6.5 mm. Specific examples of core/shell structure dimensions include, without limitation: core diameter 1.7 mm, shell thickness 0.6 mm, length 4.5 mm; core diameter 1.9 mm, shell thickness 0.9 mm, length 4.5 mm; core diameter 1.7 mm, shell thickness 0.6 mm, length 5.5 mm; and core diameter 1.9 mm, shell thickness 0.9 mm, length 5.5 mm.

The inactive region of a core-type pellet or a shell-type pellet, whether shell or core, is composed of a bioerodible excipient composition as described earlier herein, with the inactive region containing less than about 20 wt. %, e.g., less than about 10 wt. %, of the total amount of active agent in the pellet. The pharmacologically active region of a core-type pellet or a shell-type pellet, i.e., the region containing at least about 80 wt. % (e.g., at least about 90 wt. %, such as 100%) of the total amount of active agent in the pellet, may be entirely composed of the active agent, but is usually a mixture of a bioerodible excipient composition, as defined previously, and the active agent, where the active agent is dispersed within a matrix defined by the bioerodible excipient composition. The excipient composition of the inactive region and the excipient composition of the pharmacologically active region may or may not be the same, with respect to the number, type, and/or concentration of individual excipients.

Representative examples of shell and core drug delivery systems of the invention include, without limitation, the following:

Monolithic pellets 1.7 mm in diameter and 4.0 mm in length, containing 85 wt. % cholecalciferol;

Monolithic pellets 1.7 mm in diameter and 4.0 mm in length, containing 85 wt. % naproxen;

Monolithic pellets 1.7 mm in diameter and 4.0 mm in length, containing 85 wt. % methocarbamol;

Monolithic pellets 1.7 mm in diameter and 4.0 mm in length, containing 85 wt. % acetaminophen;

Monolithic pellets 1.7 mm in diameter and 4.5 mm in length, containing 95 wt. % cholecalciferol;

Monolithic pellets 1.7 mm in diameter and 4.5 mm in length, containing 95 wt. % naproxen;

Monolithic pellets 1.7 mm in diameter and 4.5 mm in length, containing 95 wt. % methocarbamol;

Monolithic pellets 1.7 mm in diameter and 4.5 mm in length, containing 95 wt. % acetaminophen;

Monolithic pellets 1.7 mm in diameter and 3.5 mm in length, containing 75 wt. % cholecalciferol;

Monolithic pellets 1.7 mm in diameter and 3.5 mm in length, containing 75 wt. % naproxen;

Monolithic pellets 1.7 mm in diameter and 3.5 mm in length, containing 75 wt. % methocarbamol;

Monolithic pellets 1.7 mm in diameter and 3.5 mm in length, containing 75 wt. % acetaminophen;

Monolithic pellets 2.8 mm in diameter and 5.5 mm in length, containing 85 wt. % cholecalciferol;

Monolithic pellets 2.8 mm in diameter and 5.5 mm in length, containing 85 wt. % naproxen;

Monolithic pellets 2.8 mm in diameter and 5.5 mm in length, containing 85 wt. % methocarbamol;

Monolithic pellets 2.8 mm in diameter and 5.5 mm in length, containing 85 wt. % acetaminophen;

Monolithic pellets 2.8 mm in diameter and 6.0 mm in length, containing 95 wt. % cholecalciferol;

Monolithic pellets 2.8 mm in diameter and 6.0 mm in length, containing 95 wt. % naproxen;

Monolithic pellets 2.8 mm in diameter and 6.0 mm in length, containing 95 wt. % methocarbamol;

Monolithic pellets 2.8 mm in diameter and 6.0 mm in length, containing 95 wt. % acetaminophen;

Monolithic pellets 2.8 mm in diameter and 5.5 mm in length, containing 75 wt. % cholecalciferol;

Monolithic pellets 2.8 mm in diameter and 5.5 mm in length, containing 75 wt. % naproxen;

Monolithic pellets 2.8 mm in diameter and 5.5 mm in length, containing 75 wt. % methocarbamol;

Monolithic pellets 2.8 mm in diameter and 5.5 mm in length, containing 75 wt. % acetaminophen;

Monolithic pellets 2.8 mm in diameter and 4.5 mm in length, containing 85 wt. % cholecalciferol;

Monolithic pellets 2.8 mm in diameter and 4.5 mm in length, containing 85 wt. % naproxen;

Monolithic pellets 2.8 mm in diameter and 4.5 mm in length, containing 85 wt. % methocarbamol;

Monolithic pellets 2.8 mm in diameter and 4.5 mm in length, containing 85 wt. % acetaminophen;

Monolithic pellets 2.8 mm in diameter and 4.0 mm in length, containing 75 wt. % cholecalciferol;

Monolithic pellets 2.8 mm in diameter and 4.0 mm in length, containing 75 wt. % naproxen;

Monolithic pellets 2.8 mm in diameter and 4.0 mm in length, containing 75 wt. % methocarbamol; and Monolithic pellets 2.8 mm in diameter and 4.0 mm in length, containing 75 wt. % acetaminophen.

Shell/core pellets with a core 1.6 mm in diameter, a shell 0.6 mm in thickness, and the pellet 5.5 mm in length, with the shell composed of 85 wt. % cholecalciferol, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.5 mm in length, with the shell composed of 85 wt. % naproxen, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.5 mm in length, with the shell composed of 85 wt. % methocarbamol, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.5 mm in length, with the shell composed of 85 wt. % acetaminophen, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.0 mm in length, with the shell composed of 85 wt. % cholecalciferol, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.0 mm in length, with the shell composed of 85 wt. % naproxen, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.0 mm in length, with the shell composed of 85 wt. % methocarbamol, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 5.0 mm in length, with the shell composed of 85 wt. % acetaminophen, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 4.5 mm in length, with the shell composed of 85 wt. % cholecalciferol, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 4.5 mm in length, with the shell composed of 85 wt. % naproxen, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 4.5 mm in length, with the shell composed of 85 wt. % methocarbamol, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 4.5 mm in length, with the shell composed of 85 wt. % acetaminophen, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 6.0 mm in length, with the shell composed of 85 wt. % cholecalciferol, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 6.0 mm in length, with the shell composed of 85 wt. % naproxen, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 6.0 mm in length, with the shell composed of 85 wt. % methocarbamol, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 6.0 mm in length, with the shell composed of 85 wt. % acetaminophen, 12 wt. % cholesterol, and 3 wt. % phosphatidylcholine, and the core composed of 97 wt. % cholesterol and 3 wt. % phosphatidylcholine;

Shell/core pellets with a core 1.6 mm in diameter, a shell 0.6 mm in thickness, and the pellet 4.5 mm in length, with the core composed of 85 wt. % cholecalciferol, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.5 mm in length, with the core composed of 85 wt. % naproxen, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.5 mm in length, with the core composed of 85 wt. % methocarbamol, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.5 mm in length, with the core composed of 85 wt. % acetaminophen, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.0 mm in length, with the core composed of 85 wt. % cholecalciferol, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.0 mm in length, with the core composed of 85 wt. % naproxen, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.0 mm in length, with the core composed of 85 wt. % methocarbamol, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 4.0 mm in length, with the core composed of 85 wt. % acetaminophen, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 5.0 mm in length, with the core composed of 85 wt. % cholecalciferol, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 5.0 mm in length, with the core composed of 85 wt. % naproxen, 12 wt. % cholesterol, and 3 wt. % phosphatidylcholine, and the shell composed of 97 wt. % cholesterol and 3 wt. % phosphatidylcholine;

Shell/core pellets with a core 1.6 mm in diameter, a shell 0.6 mm in thickness, and the pellet 5.0 mm in length, with the core composed of 85 wt. % methocarbamol, 12 wt. % cholesterol, and 3 wt. % phosphatidylcholine, and the shell composed of 97 wt. % cholesterol and 3 wt. % phosphatidylcholine; and Shell/core pellets with a core 1.6 mm in diameter, a shell 0.6 mm in thickness, and the pellet 5.0 mm in length, with the core composed of 85 wt. % acetaminophen, 12 wt. % cholesterol, and 3 wt. % phosphatidylcholine, and the shell composed of 97 wt. % cholesterol and 3 wt. % phosphatidylcholine.

In one embodiment, the tail period is at most about 12 months, preferably at most about 9 months, more preferably at most about 6 months, and ideally at most about 3 months. This contrasts with tail periods observed with prior implants, such as those described by Raymond et al. (1996) *Fertil. Steril.* 66(6):954-61), illustrated in FIG. 1 (prior art).

Various parameters can be adjusted to alter one or more other aspects of a pellet's pharmacokinetic profile, such aspects including, by way of example, release rate, release profile, duration of the extended drug delivery time period, and duration of the tail period. For instance, the rate of drug release can be controlled both by modulating the aqueous solubility of the pellet composition and by controlling the surface area of the pellet, as it is the pellet surface that is exposed to in vivo erosive forces. With monolithic implants, narrower and longer pellets generally have a shorter tail period. Monolithic thin pellets with length-to-width ratios (i.e., length-to-radius ratios for substantially cylindrical pellets) greater than about 5:1 provide for a gradual, evenly decreasing release rate. The release rate of active agent from a monolithic pellet can be controlled by the bioerosion rate of the excipient composition, made tunable using excipients with different aqueous solubilities, as alluded to earlier herein. That is, an excipient composition composed entirely of a lipidic material such as cholesterol will tend to bioerode more slowly than an excipient composition composed of a mixture of cholesterol and a second excipient having higher aqueous solubility, e.g., a selected phospholipid. The rate of release can thus be controlled by varying the relative amounts of a more water-soluble excipient and a less water-soluble excipient in an excipient composition.

For substantially cylindrical core/shell pellets composed of a slowly dissolving core and a more quickly dissolving shell that contains most or all of the active agent, the drug release profile abruptly ends as erosion from the lateral face breaks through to the underlying core. Unlike monolithic pellets, the exposed surface area of the drug-containing shell approaches a non-zero value as it erodes, thus avoiding the release tail. In these drug-containing shell pellets, the rate of drug release is controlled by the rate of shell bioerosion and by the pellet length. The duration of drug release is controlled by the shell thickness.

Placing the active agent in the core instead of the shell can also eliminate the tail if the rate of core erosion is significantly faster than that of the shell. Here, the exposed drug-containing surface is only at the cylinder bases and drug release remains relatively constant until the core erodes out of the longer-lasting shell. The shell and core release rates are tuned with the proper addition of a lipid with higher aqueous solubility than cholesterol per se, so that erosion from the lateral face of the shell does not allow breakthrough before the pellet core is fully released. To achieve this result, the shell thickness divided by the shell erosion rate must be greater than or equal to the core length divided by the core erosion rate. In these drug-containing core systems, the rate of drug release is dependent upon the rate of core dissolution and the surface area of the core bases, and the duration of release is controlled by the pellet length. An additional benefit of a drug-containing core can be approximately zero-order drug release.

IV. Male Contraception:

In administering an active agent combination to male subjects to provide long-term contraception, one or more subdermally implantable pellets are manufactured containing a combination of a progestogen and an androgen, as explained in Part II of this Detailed Description. At the outset, the number of pellets to be implanted is determined, taking into account the particular active agents, the predetermined release rate, the intended drug delivery time period, and other factors within the knowledge of the medical practitioner prescribing or administering the contraceptive system.

The pellet or pellets are then subdermally implanted, usually in the upper arm, forearm, or thigh, and allowed to remain in place. Since the pellets are bioerodible, there is no need for surgical removal, although the pellets can be surgically removed, if desired, at some point prior to complete bioerosion. The male subject is generally human, but these contraceptive implants can also be used in non-human animals.

V. Other Methods of Use:

The bioerodible, implantable pellets of the invention are useful in providing controlled release delivery of a pharmacologically active agent to patients for any purpose for which the incorporated active agent is intended.

As one example, the present drug delivery system is useful in treating a subject who requires chronic dosing with an antipsychotic medication, such as a subject suffering from bipolar disorder or schizophrenia. Chronic drug therapy in this context has been associated with very low patient compliance, especially when an individual's mood improves and patients may no longer feel they need the medication. Non-adherence is the most important predictor of re-hospitalization for psychotic disorders. The present drug delivery system eliminates the problem of patient compliance insofar as chronic administration, i.e., administration throughout an effective drug delivery period that can be as long as four years or more, precludes the need for regular self-administration by patients. Exemplary antipsychotic agents for administration to patients using the delivery system of the invention include, without limitation, haloperidol, haloperidol decanoate, iloperidone, flupenthixol, flupenthixol decanoate, paliperodone, olanzapine, aripiprazole, pipoxanthine, zuclopenthixol (preferably as the decanoate, acetate, or dihydrochloride), lithium, risperidone, valproic acid, sodium valproate, and lamotrigine, with haloperidol and risperidone particularly preferred as explained in Part II of this Detailed Description.

Compliance problems have also been noted in antiviral therapy, and particularly with antiretroviral therapy, as dosing regimens are complicated, often involving multiple active agents administered at different times throughout the day. In the management of HIV/AIDS, for instance, current options involve regular dosing with at least three different medications belong to at least two classes of antiretroviral agents: a non-nucleoside reverse transcriptase inhibitor (NNRTI) such as efavirenz, nevirapine, delavirdine, etravirine, or rilpivirine; plus two nucleoside analog reverse transcriptase inhibitors, such as zidovudine (AZT), didanosine (ddI), zalcitabine (ddC), stavudine (d4T), tenofovir (TDF), lamivudine (3TC), and/or emtricitabine. At some point in disease progression, or as the aforementioned regimen loses effectiveness, the dosing regimen is further changed or complicated by addition of a protease inhibitor to the combination or substitution of a protease inhibitor for one of the active agents. As above, using the implantable pellets of the invention to deliver these drug combinations at required levels on a long-term basis precludes the need for regular self-administration by patients and therefore eliminates all risk of non-compliance.

In another example of an area in which the present invention fulfills a significant need, the present drug delivery systems are used in the long-term administration of anti-inflammatory agents, for example in the treatment of a chronic arthritic condition, an immune system disorder such as systemic lupus erythematosus, or other conditions, disorders, or diseases responsive to ongoing anti-inflammatory therapy. The possibility of patient compliance problems is eliminated, and the adverse effects commonly seen with orally administered anti-inflammatory medications are avoided. The present systems can be used with a host of anti-inflammatory agents, including, without limitation, those incorporated into the implants prepared in the Examples (naproxen and acetaminophen).

As another example, the present drug delivery system is useful in treating a subject suffering from epilepsy and in need of anti-convulsive therapy. One of the more commonly prescribed anti-convulsant drugs, carbamazepine, an active agent that is associated with erratic oral absorption and contra-indicated for patients with gastrointestinal conditions and disorders. Administering carbamazepine using the present system would avoid the adverse effects associated with oral administration while still providing an effect dose over an extended drug delivery period.

As a further example, the invention finds utility in the treatment of many different types of cancer by providing a means for long-term administration of any of a number of different classes of anti-cancer agents. It may be advantageous, in some instances, to implant the drug delivery pellet near a tumor, so that the tumor benefits from higher concentrations of anti-cancer agent in the region of the implant. This is particularly useful with tumors that tend to respond poorly to systemic chemotherapy, such as sarcomas, particularly osteosarcomas, brain cancers, and prostate cancers. Examples of anti-cancer agents incorporated into the drug delivery pellets in this context include, without limitation, 5-fluorouracil, paclitaxel, cyclophosphamide, and thalidomide. In an approach to treating male hormone cancers such as prostate cancer, the pellets of the invention can be used in the long-term administration of leuprolide acetate, and LHRH agonist, a drug that is commonly prescribed for at least a year. Leuprolide acetate implants can also be used to treat breast cancer, endometriosis, uterine fibroids, and early puberty, by reducing a subject's testosterone levels. Treatment of female hormone cancers, such as breast cancer, cervical cancer, uterine cancer, and the like, is also simplified with the present systems insofar as commonly prescribed drugs for these cancers—such as aromatase inhibitors (e.g., letrozole and arimidex) and estrogen receptor blockers (such as tamoxifen)—are currently taken orally on a daily basis for five to ten years.

As a further example, the invention is useful for the chronic administration of vitamins, supplements that many people do not consider important and therefore fail to take as necessary. Fat soluble vitamins such as Vitamin D and Vitamin K2 are of particular interest, insofar as patients taking statins (i.e., HMG CoA reductase inhibitors prescribed as antihyperlipidemic agents or for other indications) may have reduced K2 levels (statins reduce production of K2 by the body), and many people are deficient in K2 for other reasons, and also deficient in Vitamin D. Both are important to treat and/or prevent atherosclerosis, osteopenia, osteoporosis, and other conditions; for instance, it has recently been reported that pregnant women with low Vitamin D levels are at an elevated risk for conceiving a child with autistic traits.

Accordingly, the subdermally implantable pellets of the invention are useful in providing for the ongoing, controlled release of a pharmacologically active agent for a host of indications with a wide variety of active agents and active agent classes. It is to be understood that the invention is not limited to the conditions, disorders, diseases, and active agents explicitly mentioned herein, and that other specific agents and indications with which the present invention is useful will be apparent to those of ordinary skill in the art and/or are described in the relevant texts and literature.

VI. Pellet Implantation:

One or more controlled release pellets of the invention are subdermally implanted into a subject for long-term, sustained release administration of the pharmacologically active agent therein, as described throughout this specification. Generally, although not necessarily, the drug-containing pellets are positioned just under the skin. Methods and devices for insertion and positioning of subdermal implants are known in the art, and any suitable method or device can be used in conjunction with the invention. Examples of suitable implantation devices include trocar-like inserters, other commercially available implantation devices, and devices described in the patent literature such as in U.S. Pat. Nos. 4,223,674; 6,964,648; 7,214,206; 7,510,549; 7,850, 639; and International Patent Publication No. WO 98/13092 A1. Other suitable implantation devices will be apparent to those skilled in the art and/or are described in pertinent texts and literature. Subdermal implantation methods and devices should be non-irritating and non-sensitizing, and should work relatively quickly.

VII. Pellet Manufacture:

Any method to manufacture the present pellets may be implemented so long as the compositional and physical requirements of the pellets so made are met. Manufacturing methods include, for example, compression molding, molding, hot melt extrusion, injection molding, and hot melt molding.

One example of a preferred method to manufacture the present pellets is a variation of the hot melt molding process, a hot melt "drawing" process that uses a pin to pull a substantially homogenous mixture of pellet substrate material out of a heated reservoir and into a heated channel, or tube, composed of an inert, heat-resistant material such as polytetrafluoroethylene ("PTFE"). The pellet material can then be cooled under "channel capping" conditions, i.e., conditions that allow the pellet to fully form without internal cavities or sinks. Channel capping involves withdrawal of the elongated pin from the interior of the formed pellet, when still warm, in a gradual manner that allows the interior of the pellet to fuse and contract.

The method can be modified to make core-type and shell-type pellets, by first drawing molten shell material from the reservoir into the channel and allowing it to harden somewhat, forming a shell between a narrow pin extension and the interior of the channel. After allowing some cooling, and wiping the reservoir clean before continuing, molten core material from the reservoir is then drawn into the solidified shell. After a brief cooling period, the solid core-and-shell pellet can be pushed out of the channel/tube.

Figure 2A:
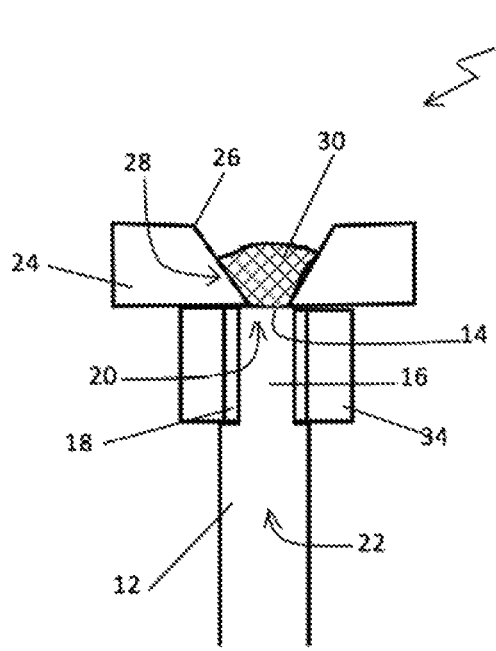
FIG. 2A schematically illustrates a pellet manufacturing assembly used to make a monolithic pellet of the invention, prior to drawing the pellet composition into the pelleting tube.
Figure 2B:
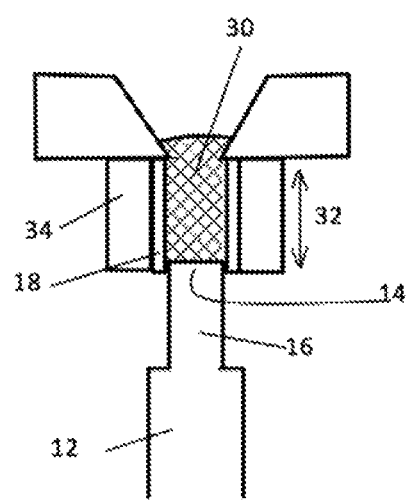
FIG. 2B schematically illustrates the pellet manufacturing assembly subsequent to drawing the pellet composition into the pelleting tube.

FIG. 2A and 2B illustrate a pellet manufacturing assembly that can be used to make monolithic pellets of the invention. As shown in FIG. 2A, the assembly 10 includes an elongated pin having a body 12, a tip 14, and a substantially cylindrical upper segment 16. The pin is used in conjunction with pelleting tube 18, which has an upper tube opening 20, an opposing lower tube opening 22, and an inner surface. Tube 18 has an inner diameter sized to provide a sealing fit between the inner surface and the upper segment of the pin. The assembly further includes a funnel 24 in the form of an inverted cone structure concentrically tapering from an upper rim 26 down to a narrow outlet 28 aligned with the upper tube opening 20. It will be appreciated that the a functionally equivalent reservoir can be substituted for the funnel, providing that the reservoir is large enough to contain the intended volume of the selected pellet composition and has an outlet that enables downward flow of the pellet composition in a molten state. The funnel and tube are therefore in fluid communication so that the flowable pelleting material can enter the tube from the funnel.

To manufacture a pellet, the pin tip 14 is inserted into tube 18 through lower tube opening 22, and the pin is then moved upward through the tube toward the funnel until the pin tip reaches the upper tube opening; the pin is shown positioned in this manner in FIG. 2A. At that point, the upper tube opening having been sealed with the upper segment of the pin, the pellet composition 30, containing a pharmacologically active agent, is placed into the funnel. The pellet composition may be placed into the funnel in molten, i.e., flowable, form, or it can be heated within the funnel until rendered flowable if a temperature control mechanism is operably connected to the funnel body. The pin is then partially withdrawn from the tube through the lower tube opening, such that the pin tip is lowered a selected distance 32 from the upper tube opening, as illustrated in FIG. 2B.

This draws the molten pellet composition 30 down into the tube via a siphoning effect. After the pin tip has been lowered, the pellet composition is allowed to cool so as to form the hardened pellet within the tube. The pin is then completely removed from the tube, and the pellet removed using any suitable means. The pellet so formed has a pellet length corresponding to the distance that the pin tip is lowered, i.e., the "selected distance," and a pellet diameter defined by the inner diameter of the pelleting tube. In a preferred embodiment, the assembly includes a means for maintaining the pelleting tube in place, such as the collar 34 shown in FIGS. 2A and 2B.

Figure 3D:
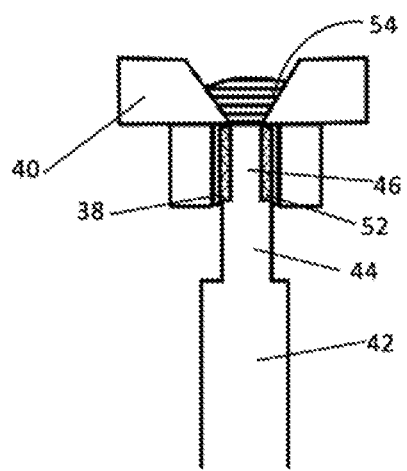
FIG. 3D illustrates the core-and-shell type pellet manufacturing assembly of FIG. 3C with the core composition having been introduced into the funnel above the pelleting tube.
Figure 3E:
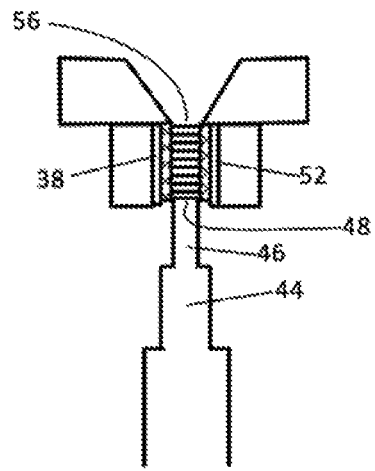
FIG. 3E illustrates the core-and-shell type pellet manufacturing assembly of FIG. 3D with the core composition having been drawn down into the cooled shell material within the pelleting tube.

To form a core-and-shell type of pellet, illustrated in FIGS. 3A through 3E, a pellet manufacturing assembly 36 includes a pelleting tube 38 and a funnel 40 as described above for monolith manufacture. In this case, however, an elongated pin 42 is used that is composed of two axially aligned, substantially cylindrical segments of different diameters that are longitudinally adjacent, with a wider lower segment 44 and a narrower upper segment 46 that terminates in the pin tip 48. In addition, the relative dimensions in this context are such that a sealing fit is provided between the inner surface of the tube and the wider, lower segment of the elongated pin, while, as indicated in FIG. 3A, the upper, narrower segment of the pin is significantly narrower than the inner diameter of the tube.

Formation of a core-and-shell pellet begins by inserting the pin tip into the lower tube opening and moving the pin upward through the tube, toward the funnel, until the pin tip and then the upper pin segment protrude from the upper tube opening into the funnel; this configuration is shown in FIG. 3A. Upward, vertical movement of the pin through the tube in this way brings the lower pin segment into the tube, with the upper tube opening sealed as a result. As the shell is made first, the shell composition 50 is then placed into the funnel; see FIG. 3B. As with monolith manufacture, the shell composition may be heated until rendered flowable prior to placement in the funnel, or it can be heated within the funnel if a suitable heating apparatus is operably connected. To make the shell, the lower pin segment is gradually withdrawn from the tube through the lower tube opening, thus lowering the upper pin segment into the tube and simultaneously drawing the flowable shell composition into the concentric space forming between the upper, narrow segment of the pin and the inner surface of the tube as the pin is lowered; see FIG. 3C. The hot shell composition is allowed to cool, thereby hardening into a shell 52 formed around the upper segment of the pin, within the tube, as shown in FIG. 3C.

The core composition 54 (see FIG. 3D) is added into to the funnel 40 after cleaning, and is either in molten, flowable form prior to placement in the funnel or heated therein, as described above. The narrower, upper pin segment 46 is then gradually lowered within the tube, drawing the core composition down into the shell; see FIG. 3E. The core-and-shell pellet so formed is allowed to cool, with the molten core 56 fusing within the shell 52 during the cooling process, and harden to a degree sufficient to allow complete removal of the pin without any flow of pelleting material. The finished pellet can then be removed from the tube using any suitable means.

The methodology allows facile control over pellet dimensions, insofar as the diameter of the pellet formed is determined by the inner diameter of the tube, and the length of the pellet is determined by the extent to which the pin or individual segments thereof are lowered within the tube, before the pellet, core, or shell is allowed to cool and harden.

It will therefore be appreciated that the method can be readily adapted to make pellets of different dimensions. That is, pellets of different diameters can be made by using a narrower or wider tube, and, correspondingly, different core diameters, while pellet length can be adjusted by lowering the pin within the tube to a lesser or greater degree as molten pellet material is drawn into the tube interior.

The above-described process for making core-and-shell pellets can be adapted to make pellets with more than one shell, by using an elongated pin with multiple segments and segment-by-segment step-wise lowering of the pin within the tube, as each shell is made and allowed to harden within the pelleting tube.

Channel capping, as explained earlier in this section, facilitates pellet formation in a manner that allows the interior pellet to fuse and contract without formation of internal cavities or sinks. This is done, in part, by lowering the pin within the tube in a gradual manner, and in part by allowing a small amount of pelleting composition to remain in the funnel just above the funnel-tube junction.

In a preferred approach, channel capping is carried out in shell formation, core formation, or, more preferably, both. Following completion of pellet manufacture, the completed pellet is released using any effective method.

It should be noted that the invention is not limited with respect to the aforementioned methods of manufacture, and that other methods for making the pellet implants are possible, including modified versions of the aforementioned methods or entirely different methods known to those of ordinary skill in the art.

To scale up pellet manufacture, it will be appreciated that automation of one or more aspects of the method is desirable. For example, an automated pin positioning means would be useful for moving the elongated pin vertically into and through the pelleting tube and then withdrawing the pin, wherein the pin would be withdrawn stepwise in a core-and-shell manufacturing method such as that described above. As another example, an automated means for filling the funnel or a functionally equivalent reservoir with pelleting material, including shell material and core material, would be desirable, as would a reservoir cleaning technique and a pellet removal system. Other such automated means will be apparent to those of ordinary skill in the art and/or are described in the pertinent texts and literature.

It is to be understood that while the invention has been described in conjunction with a number of specific embodiments, the foregoing description as well as the examples that follow are intended to illustrate and not limit the scope of the invention. Other aspects, advantages and modifications will be apparent to those skilled in the art. All patents, patent applications, and publications mentioned here are hereby incorporated by reference in their entireties.

EXPERIMENTAL

General Procedure A—Monolithic Pellet Manufacture:

Subdermally implantable monolithic pellets of the invention were prepared in these examples using a hot melt method, as described below.

System preparation: A funnel as illustrated in the hot melt molding system of FIG. 2A and 2B was heated to a temperature just high enough to render the pellet composition flowable. A length of PTFE tubing, cut to allow a seal to form between the heated funnel and the tubing, was placed into a heated collar to bring the temperature to just below the transition temperature of the powder, i.e., the temperature at which the powder transforms from a substantially solid form into a flowable form. The collar, with PTFE tube attached, was placed on a drawing pin such that the pin extended through the length of the tube, terminating just below the funnel. The pin is sized such that its diameter is sufficiently close to the inner diameter of the PTFE tube to provide a sealing fit therebetween. The funnel was then brought into contact with the top of the heated collar and therefore with the pin as well, such that the channel's opening was aligned with the center of the pin, collar and tube. This arrangement created a seal between the channel's opening and the upper region of the PTFE tubing.

Materials: cholesterol; phosphatidylcholine or lecithin; and etonogestrel.

Monolithic pellet preparation: All materials were fully dissolved in ethanol, and the ethanol was then evaporated to leave a homogeneous composition of the pellet components as a powder. These materials may, alternatively, be slurried by hand or machine mixing in any USP grade organic solvent, with ethanol preferred. In formulations with free-flowing dry powders, dry-mixing equipment, such as V-blenders or other type of blenders, may be used.

The powdery pellet composition was poured directly into the heated funnel. The amount of material added to the funnel was calculated to provide enough material to fill the PTFE tubing cavity as well as create a residual in the funnel that capped off the PTFE tubing, thereby causing a complete fill of the cavity and preventing air from entering and creating voids and cracks in the pellet. As the powdered material reached its transition temperature and became flowable, the pin was lowered through the PTFE tubing, drawing the pellet composition into the tube and forming an elongated rod.

Pellet post processing: The rod was allowed to cool in ambient conditions in place for approximately 30 to 60 seconds prior to removing the collar and PTFE tube for cooling at room temperature. Once the rod cooled, it was ejected from the PTFE tube with a pin and inspected. It was then available for trimming to predetermined pellet dimensions using a hot knife.

General Procedure B—Manufacture of Core-and-Shell Pellets, Drug-Containing Core ("Core-Type Pellets"):

Modifications were made to the above procedure for making monolithic pellets in order to make core-and-shell pellets, i.e., subdermally implantable pellets with a drug-containing core in an inert shell. The pellet manufacturing assembly used to make core-and-shell pellets is schematically illustrated in FIGS. 3A through 3E.

System preparation: The hot melt molding system was set up and readied for pellet manufacture as described above with respect to monolithic pellets.

Materials for the drug-containing core: cholesterol; phosphatidylcholine and/or lecithin; and etonogestrel.

Materials for the inert shell: lipid only, e.g., cholesterol and/or phosphatidylcholine.

Preparation: All core materials were fully dissolved in ethanol, and the ethanol was then evaporated to leave a homogeneous composition of the core components as a powder. Shell materials were slurried in ethanol, and the ethanol was then evaporated to leave a homogeneous composition of the shell components as a powder.

In this case, in contrast to monolith manufacture, as described in General Procedure A, a double pin was used to fabricate the core-and-shell pellet in two stages. The double pin was made by assembling a narrower pin on top of and in axial alignment with the somewhat wider pin used for monolith preparation, the narrower pin forming an extended narrower segment of an integral pin structure comprised of two segments of different diameter.

The powdery shell composition was poured directly into the heated funnel. The amount of material added to the funnel was calculated to provide enough material to fill the PTFE tubing cavity, with the narrower pin segment container therein, and create a residual in the funnel that capped off the PTFE tubing. This resulted in complete filling the cavity and preventing air from entering and creating voids and cracks in the shell. As the powdered material in the heated funnel began to coalesce and flow, the pin was lowered through the PTFE tubing, drawing the flowable shell material, along with the extended narrower segment of the pin, into the tube and forming an elongated cylinder around the narrower pin segment. The cylinder thus formed was composed of the shell composition and serves as the shell of the final pellet. To form the core, the funnel was wiped clean of shell material and the mixed core powder was then added into the funnel. After heating the core composition until flowable, the pin was drawn down a second time, so that the narrower upper segment was withdrawn almost completely from the solidified shell. The tight contact between the shell and pin, and between the tube and funnel, resulted in a partial vacuum as the pin is withdrawn from the shell, thereby siphoning flowable core material from the funnel into the shell. The core was allowed to cool and harden within the shell. The tube was then removed from the apparatus and the core-and-shell pellet allowed to further cool at room temperature before being extracted from the tube.

General Procedure C—Manufacture of Core-and-Shell Pellets, Drug-Containing Shell ("Shell-Type Pellets"):

Core-and-shell pellets with a drug-containing shell and an inert core (i.e., "shell-type pellets) were manufactured using the process of General Procedure B, except that the drug-containing material was added to the funnel first to form the shell, and the inert material added second to form the core.

Unless otherwise indicated, all percentages herein are weight % (wt. %), all ratios are weight ratios, and all width and length measurements are in millimeters.

Example 1

Monolithic Pellets: Effect of Pellet Diameter on Release Rate and Duration

Rod-shaped, substantially cylindrical monolithic pellets, having identical compositions but differing in diameter, were made using General Procedure A.

Composition: 85 wt. % etonogestrel ("ENG"), 3 wt. % phosphatidylcholine ("PC"), and 12 wt. % cholesterol ("CH").

The pellets made were both 4 mm in length, with one pellet having a diameter of 1.7 mm (a "monolithic thin" type of pellet) and the other pellet having a diameter of 2.8 mm (a "monolithic thick" type of pellet). Drug release rate in 95.0% denatured ethanol (i.e., anhydrous ethanol denatured with 5 vol. % methanol and 5 vol. % isopropanol) and 5% deionized water was evaluated over a time period of about 30 minutes, as follows:

50.0 ml of the 95.0% ethanol dissolution medium were added to a 125 mL Erlenmeyer flask, which was then sealed with paraffin film. Two capillary tubes were inserted through the film and into the dissolution medium, and were connected to a peristaltic pump that circulated the solution at 4 mL/min through a 0.2 mm path length quartz cuvette in a UV-Vis spectrometer. The pellet was dropped into the dissolution medium, which was stirred at room temperature in the flask on an orbital shaker set to 150 rpm. The absorbance was measured at 240 nm, as ENG absorbs strongly at that wavelength while the excipients, CH and PC, do not. Absorbance measurements were taken at 1-second intervals for 15 to 180 minutes until the spectrometer response remained constant, indicating complete dissolution of the pellet.

Figure 4:
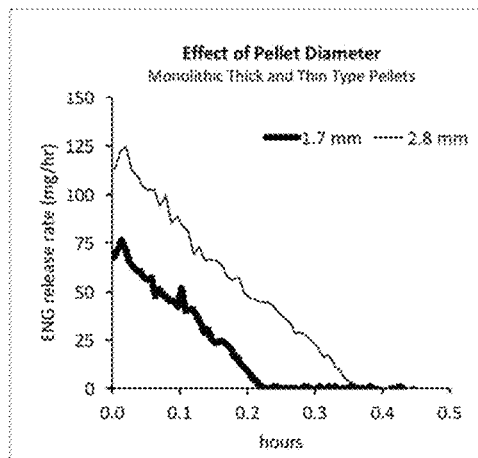
FIG. 4 provides the dissolution profiles for monolithic pellet implants with different diameters, as described in Example 1.

The dissolution profiles are shown in FIG. 4. The thinner monolithic pellets clearly stopped ENG release much earlier than thicker, more traditional pellets, and they also started with a lower dose. As may be seen in the figure, increasing the pellet diameter increased both duration of drug release, i.e., the time period during which a measurable drug concentration was seen, and the drug release rate.

Example 2

Monolithic Pellets: Effect of Pellet Length on Release Rate and Release Duration Two groups of rod-shaped, substantially cylindrical monolithic pellets, having identical compositions but differing in length, were made using General Procedure A.

Composition: 85 wt. % ENG, 3 wt. % PC, and 12 wt. % CH.

Figure 5:
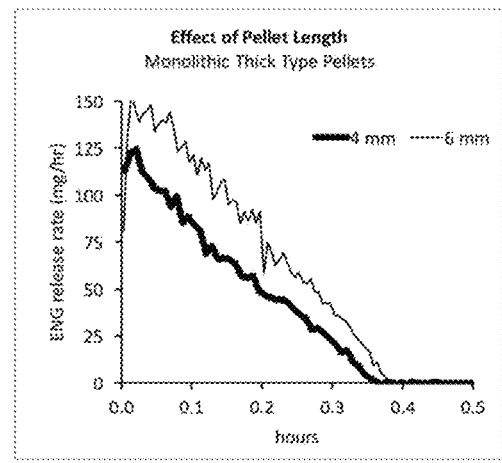
FIG. 5 provides the dissolution profiles for monolithic pellet implants with different lengths, as described in Example 2.

The pellets made were both 2.8 mm in diameter, with one pellet having a length of 4 mm and another pellet having a length of 6 mm. The dissolution profiles obtained using the methodology described in Example 1 are shown in FIG. 5. As may be seen in the figure, the two pellets released drug over a time period of similar duration, but the shorter pellets gave rise to a shallower slope for the decreasing rate of etonogestrel release, meaning that the release rate for the longer pellets decreased faster than that of the shorter pellets.

Example 3

Core-Type Pellets: Release Rate and Duration

General Procedure B was followed to prepare pellets having a core of 85 wt. % ENG, 12 wt. % CH, and 3 wt. % PC, and a shell of 97 wt. % CH and 3 wt. % PC. The diameter of each core was 1.6 mm and each shell was 0.6 mm thick, giving a total pellet diameter of 2.8 mm. Pellet length was 4 mm. Drug release over time was evaluated in 95% ethanol as described in Example 1. Results are shown in the dissolution profile of FIG. 6 (see the curve corresponding to the pellet length of 4 mm).

Example 4

Core-Type Pellets: Effect of Pellet Length on Release Rate and Duration

Figure 6:
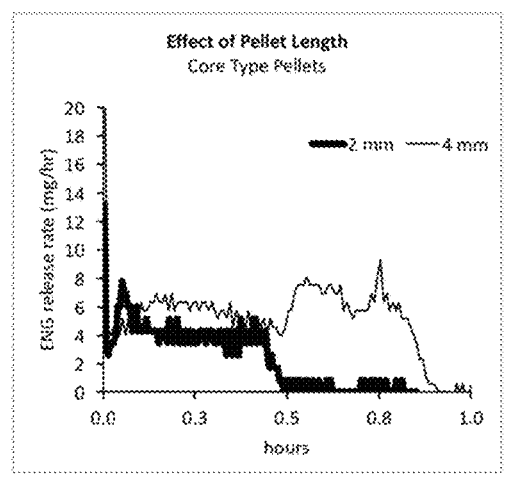
FIG. 6 provides the dissolution profile for core-type pellets, as described in Examples 3 and 4.

General Procedure B was followed to prepare core-type pellets having a core of 85 wt. % ENG, 12 wt. % CH, and 3 wt. % PC, and a shell of CH and PC in a 97:3 weight ratio. For purposes of evaluating the effect of pellet length on release rate and duration with core-type pellets, a core pellet was prepared as in Example 3, but with a pellet length of 2 mm. Drug release rate was evaluated as described in Example 1, and the dissolution profiles are shown in FIG. 6. Comparing the figure with the release profiles of the monolithic pellets shows that the ENG release rate is significantly slower with core-type pellets than with monolithic pellets. Doubling the core pellet length from 2 mm to 4 mm doubled the ENG release duration while maintaining a fairly even ENG release rate of approximately 5 mg/hr.

Example 5

Shell-Type Pellets: Effect of Pellet Length on Release Rate and Duration

Figure 7:
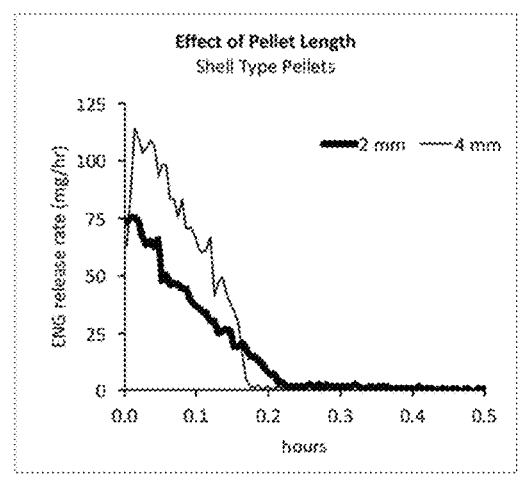
FIG. 7 provides the dissolution profiles for shell-type pellets of different lengths, as described in Example 5.

General Procedure C was followed to prepare shell-type pellets having a core of CH and PC in a 97:3 weight ratio and a shell of 85 wt. % ENG, 12 wt. % CH, and 3 wt. % PC. The diameter of each core was 1.6 mm and each shell was 0.6 mm thick. As in the preceding example, a first pellet was prepared that was 2 mm in length, and a second pellet was prepared that was 4 mm in length. Drug release rate in ethanol was evaluated as described in Example 1. The dissolution profiles for the two pellet groups are shown in FIG. 7. In this case, increasing the length of the pellet did not substantially change the duration of ENG release, but did increase ENG release rate. Shell pellets are designed to have a rapid cessation of ENG release once the shell has eroded to the CH core. This can be seen with the 4 mm shell pellet, compared to the 4 mm monolithic pellet, but was not clearly seen in the 2 mm shell pellet.

Figure 8A:
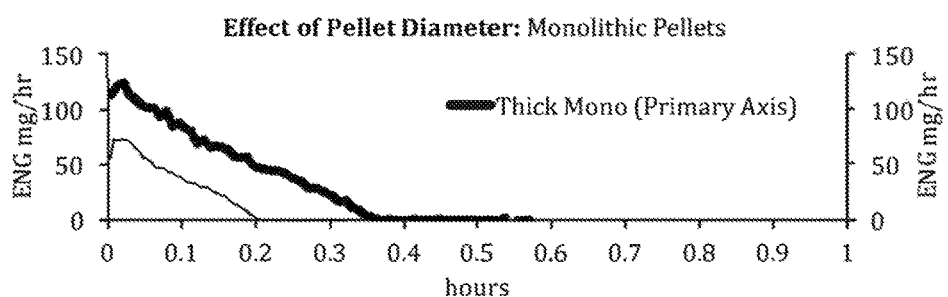
FIG. 8A shows the dissolution profiles of thin monolithic pellets compared with thick monolithic pellets as also described in Example 5.
Figure 8B:
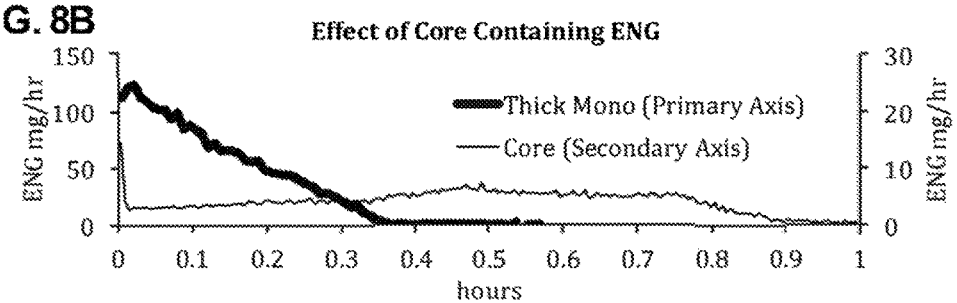
FIG. 8B shows the dissolution profiles of core-type pellets compared with thick monolithic pellets, as also described in Example 5.
Figure 8C:
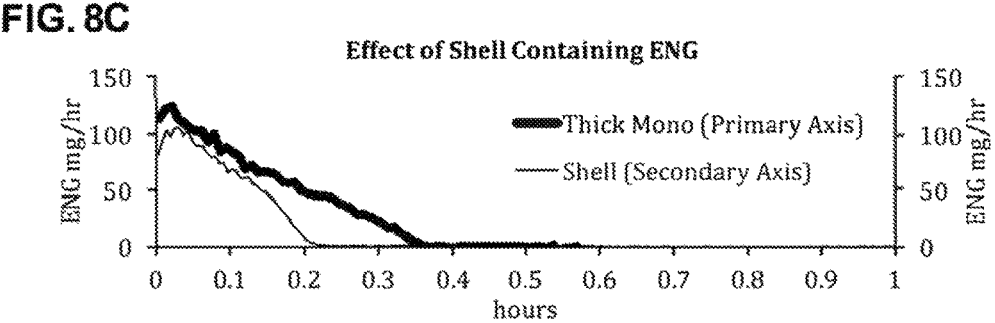
FIG. 8C shows the dissolution profiles of shell-type pellets compared with thick monolithic pellets, as also described in Example 5.
Figure 9:
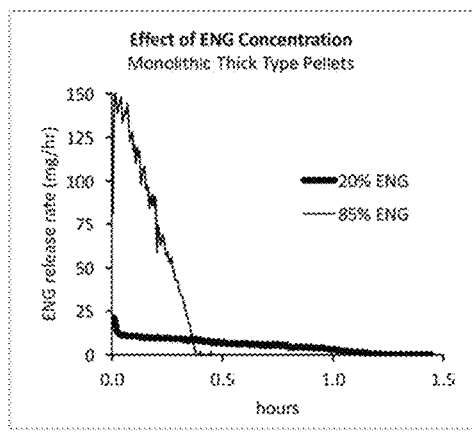
FIGS. 9 through 12 illustrate the effect of active agent concentration on release rate, in thick monolithic pellets (FIG. 9), thin monolithic pellets (FIG. 10), core-type pellets (FIG. 11), and shell-type pellets (FIG. 12), as described in Example 6.
Figure 10:
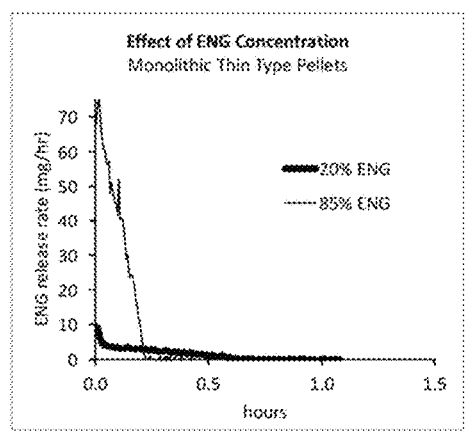
Figure 11:
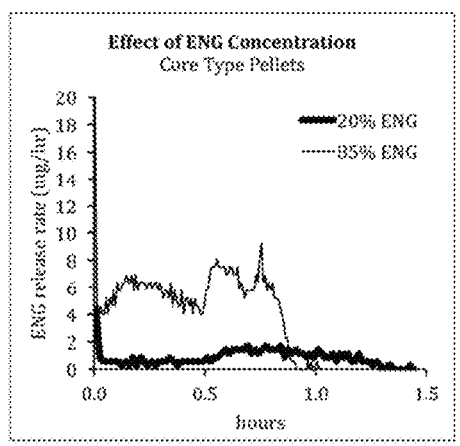
Figure 12:
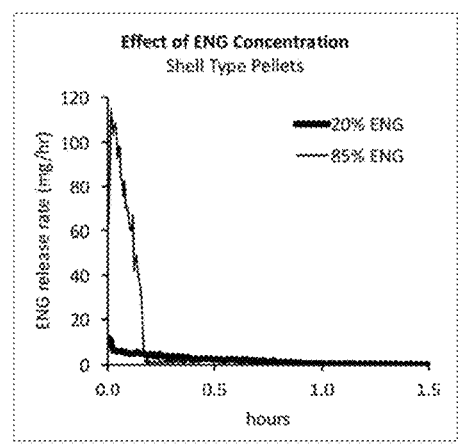
Figure 13:
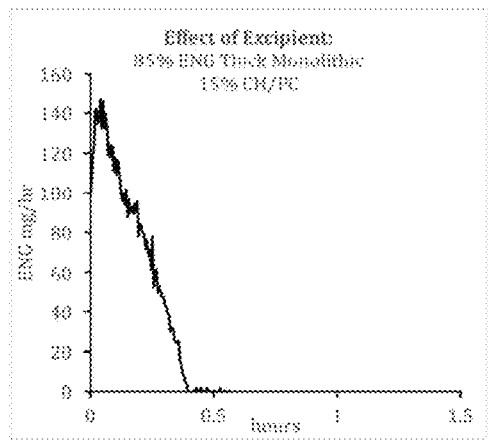
FIGS. 13 through 17 illustrate the effect of excipient selection on release rate, as described in Example 7.
Figure 14:
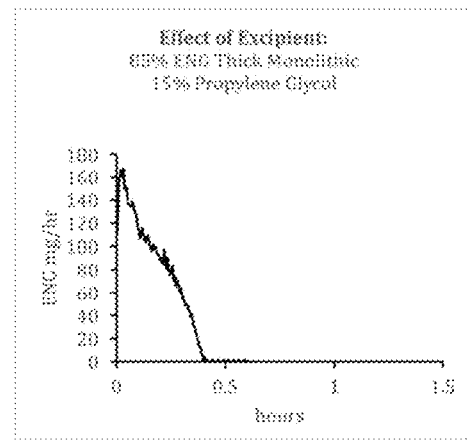
Figure 15:
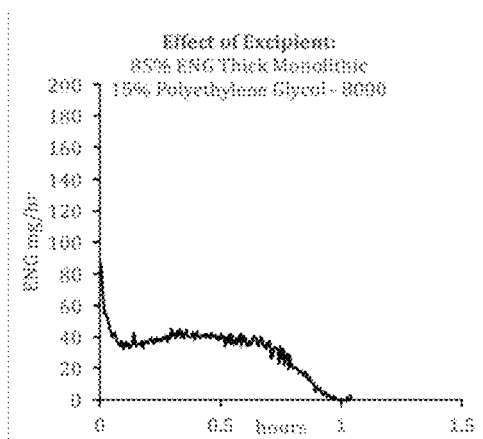
Figure 16:
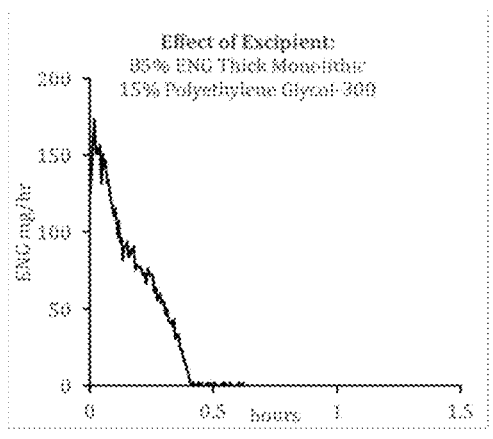
Figure 17:
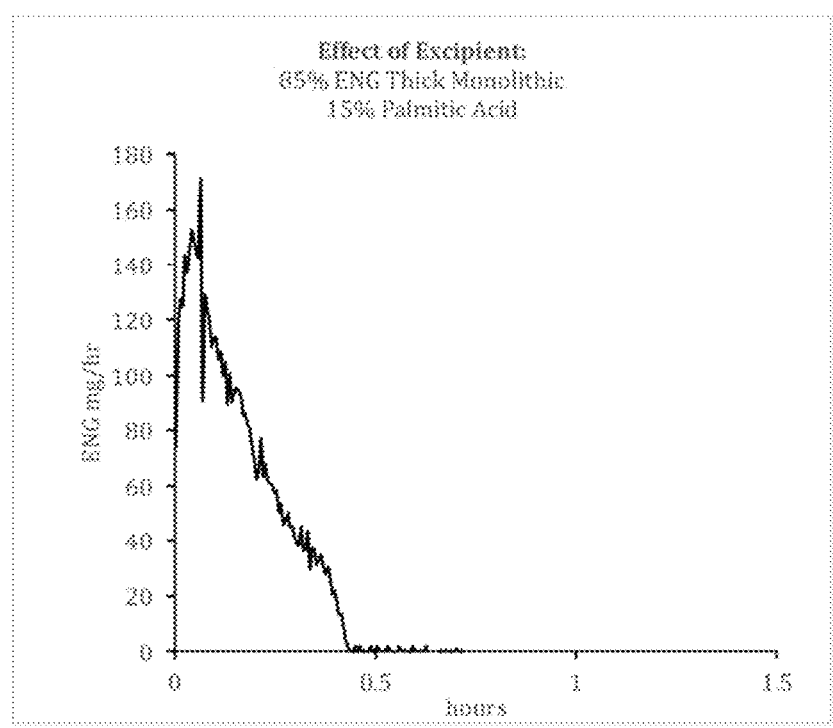

For purposes of comparison, the dissolution profiles obtained for the thick monolithic pellets and thin monolithic pellets (Example 1) are shown as a group in FIG. 8, with the dissolution profiles obtained for core-type pellets (Example 3) and shell-type pellets (Example 5), all pellets 4 mm in length. In FIG. 8, Profile A corresponds to the monolithic thick and thin pellets, Profile B corresponds to the core-type pellets, and Profile C corresponds to the shell-type pellets.

Example 6

Effect of Drug Concentration on Drug Release Profile

In order to assess the concentration of drug in the implant on the drug release profile, four types of pellets were made, with two drug concentration subgroups prepared for each of the four pellet types:

Type (I), Monolithic thick pellets. Dimensions: Diameter, 2.8 mm, length, 6 mm. Type (I), subgroup (A): 85% ENG, 12% CH, 3% PC. Type (I), subgroup (B): 20% ENG, 77% CH, 3% PC.

Type (II), Monolithic thin pellets. Dimensions: Diameter, 1.7 mm; length, 4 mm.-Type (II), subgroup (A): 85% ENG, 12% CH, 3% PC. Type (II), subgroup (B): 20% ENG, 77% CH, 3% PC.

Type (III), Core-type pellets. Dimensions: Core diameter, 1.6 mm; shell thickness, 0.6 mm; length, 4 mm. Type (III), subgroup (A): 85% ENG, 12% CH, 3% PC core and 97% CH, 3% PC shell. Type (III), subgroup (B): 20% ENG, 77% CH, 3% PC core and 97% CH, 3% PC shell.

Type (IV), Shell-type pellets. Dimensions: Core diameter, 1.6 mm; shell thickness, 0.6 mm; length, 4 mm. Type (IV), subgroup (A): 85% ENG, 12% CH, 3% PC shell and 97% CH, 3% PC core. Type (IV), subgroup (B): 20% ENG, 77% CH, 3% PC shell and 97% CH, 3% PC core.

The release rate results obtained using the method of Example 1 can be seen in the comparative release profiles of FIGS. 9 through 12. With all four pellet types, thick, thin, core and shell, the rate of ENG release increased with an increase in ENG content, while the release duration decreased with an increase in ENG content. While the approximately four-fold greater ENG content in the 85%

ENG pellets relative to the 20% ENG pellets might have been expected to give an approximately four-fold greater release rate of ENG, the EN release from the 85% pellets was, surprisingly, substantially higher than four-fold faster. ENG release from pellets with higher CH content is slowed because the aqueous solubility of a 20% ENG/80% CH solid mixture is lower than one containing 85% ENG/15% CH.

Example 7

Effect of Changing Excipient on Drug Release Profile

In order to assess the impact of a change in excipient on drug release profile from pellet implants, several monolithic pellets were made with different excipient compositions but were otherwise identical. Pellet dimensions: diameter 2.8 mm, length 6 mm. Composition: 85% ENG, 15% excipient. Pellets were made with the excipients indicated below.
Excipient 1: CH/PC at a 4:1 weight ratio.
Excipient 2: Propylene glycol (PG).
Excipient 3: Polyethylene glycol 8000 (PEG-8000).
Excipient 4: Polyethylene glycol 300 (PEG-300).
Excipient 5: Palmitic acid (PA).
Dissolution profiles obtained using the method of Example 1 are provided in FIGS. 13 through 17 for Excipients 1 through 5, respectively.

At 85% ENG, this major component, i.e., the active agent, controlled the overall release profile when relatively small molecules were used as the excipient. The addition of a large polymeric molecule, PEG-8000, was found to inhibit ENG release and increase the release duration.

Example 8

In Vivo Evaluation

Five types of pellets were prepared using the procedures of the earlier examples:
ENG thick monolithic (85% ENG, 12% CH, and 3% PC; diameter 2.8 mm, length 6 mm;
ENG thin monolithic (85% ENG, 12% CH, and 3% PC; diameter 1.7 mm, length 4 mm;
ENG shell (core of CH/PG at a 97:3 ratio; shell of 85% ENG, 12% CH, and 3% PG; core diameter 1.6 mm, shell thickness 0.6 mm, and length 4 mm;
ENG core (core of 85% ENG, 12% CH, and 3% PG; shell of CH/PC at a 97:3 weight ratio; core diameter 1.6 mm, shell thickness 0.6 mm, and length 4 mm;
NET (norethindrone) thick monolithic (85% NET, 15% CH); diameter 2.8 mm, length 6 mm.

Figure 18:
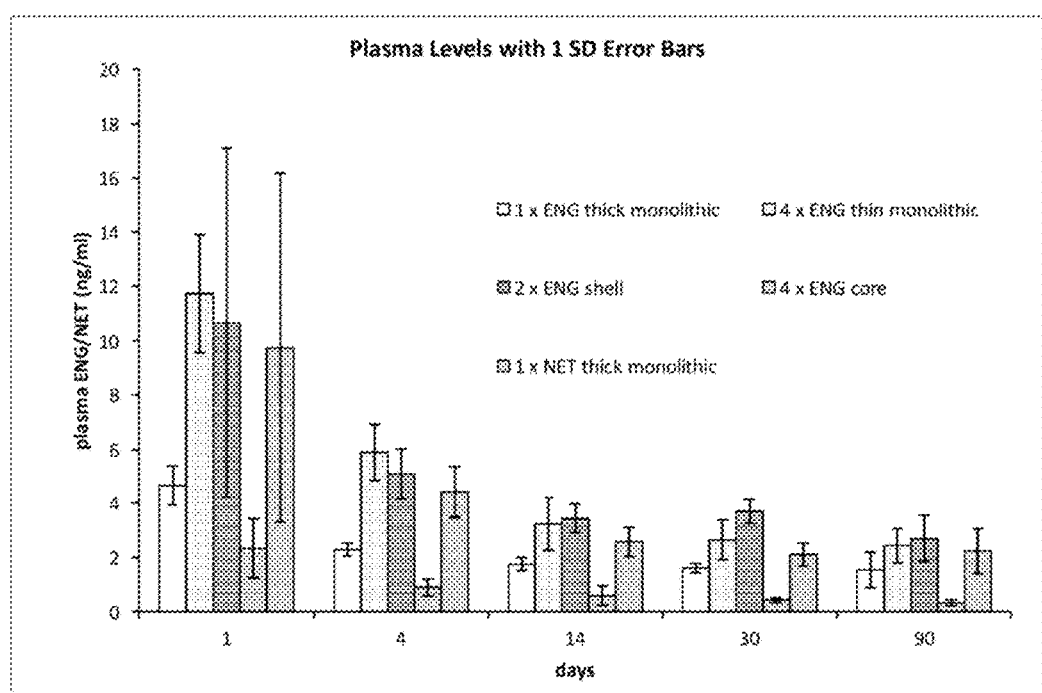
FIG. 18 illustrates the in vivo test results obtained in Example 9, showing plasma progestin levels measured at different post-implantation time points.

The five pellet types were implanted subcutaneously into eight rats per pellet type (except for NET thick monolithic, where pellet one was pulled out by the animal sometime during day 1). The number of pellets implanted per rat was chosen to keep the total ENG doses similar (32±5 mg). Pellets were implanted separately on the animal's back. Rats received a 1× ENG or NET thick monolithic pellet above one front leg, or 2× shell pellets above both front legs, or 4× thin monolithic pellets or core pellets above all four legs. Blood plasma levels were evaluated at day 1, day 4, day 14, day 30, and day 90. Extended release was achieved with all pellets, as indicated by FIG. 18.

Figure 19:
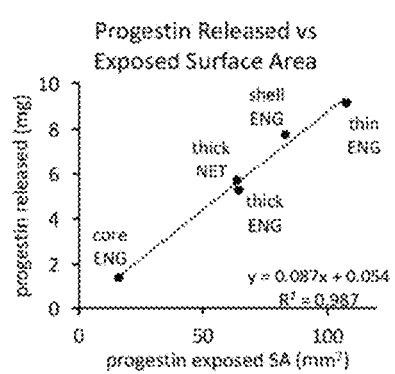
FIG. 19 shows the correlation between total drug released and the exposed surface area of drug-containing regions within the pellet, as determined in Example 8, while FIG. 20 provides the AUC (mg*day/mL) versus amount of drug released.
Figure 20:
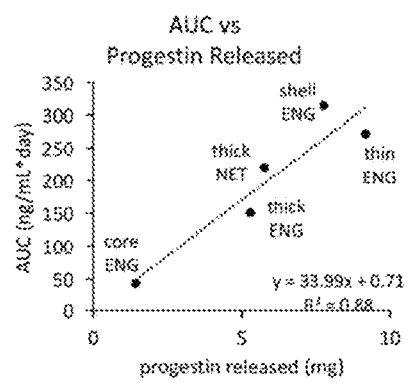

Then, the unreleased progestin per rat was averaged for each pellet type, and the amount released was calculated by difference from the average starting content based on the analysis of pellets made in the same batches as those implanted. FIG. 19 shows that the amount of progestin initially released from the pellets tightly correlates with the exposed surface area, supporting the same surface erosion mechanism in vivo as that seen in vitro, and also supporting a correlation between ENG loss and blood levels, implying that the amount of drug released and the rate of drug release can be controlled by varying exposed ENG surface area. A good correlation showing a linear dose response was found between the blood concentration integrated over the three-month exposure (i.e., the area under the curve or "AUC") and the amount of progestin released from the pellets, as seen in FIG. 20.

Example 9

Naproxen Monoliths and Core-Type Pellets

Figure 21:
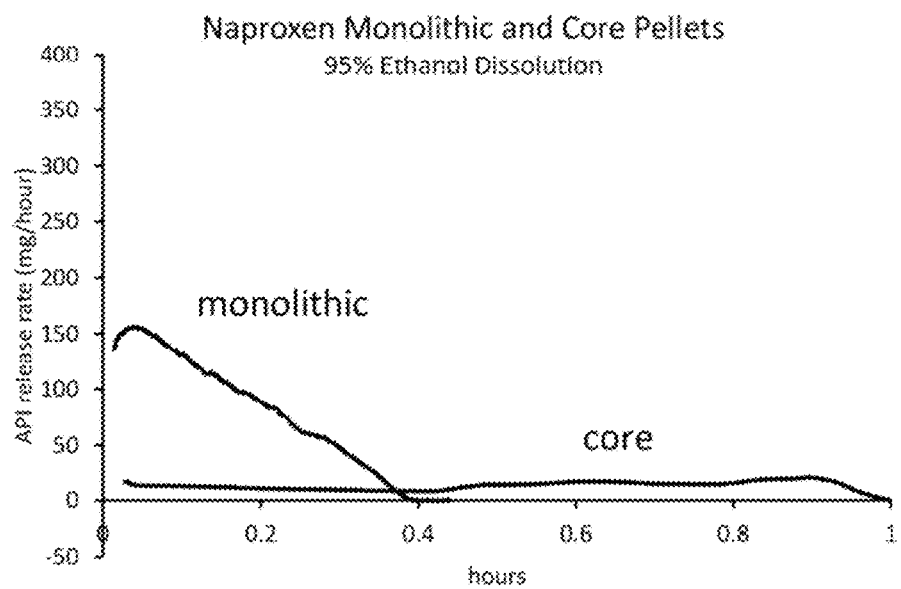
FIG. 21 shows the dissolution of monolithic pellets and core-type pellets made with naproxen, as described in Example 9.

Monolithic and core-type pellets of the invention were made with the active agent naproxen ((S)-(+)-2-(6-methoxy-2-naphthyl)propionic acid)), a non-steroidal anti-inflammatory agent with a melting point of 153° C. (obtained from VWR, in the form of the free acid). Monolithic pellets were prepared as described in General Procedure A, containing 85 wt. % naproxen, 12 wt. % cholesterol, and 3 wt. % phosphatidylcholine. Core-type pellets were prepared as described in General Procedure B, with a shell of 97 wt. % cholesterol and 3 wt. % phosphatidylcholine, and a core composition of 100% naproxen fed into the shell during pellet manufacture. Monoliths and core-type pellets were 2.8 mm in diameter, with monoliths 5.5 mm in length and core-type pellets 4 mm in length. Naproxen release from both pellet types was evaluated; results are shown in FIG. 21. As FIG. 21 indicates, the naproxen core pellet provided approximately zero-order (i.e., steady-state) release, while the naproxen monolith gave a release profile in which release rate decreased approximately linearly until the drug was depleted.

Example 10

Methocarbamol Monoliths and Core-Type Pellets

Figure 22:
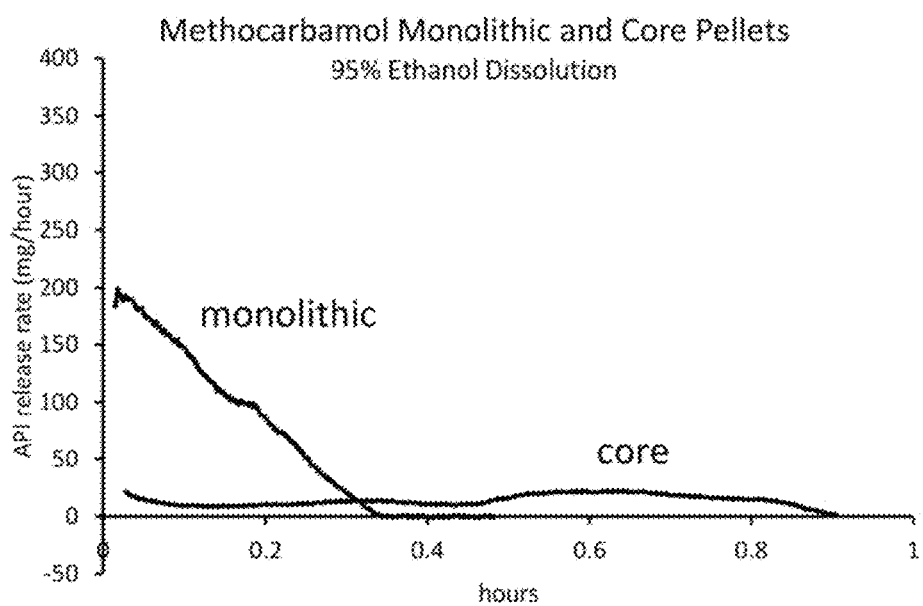
FIG. 22 shows the dissolution of monolithic pellets and core-type pellets made with methocarbamol, as described in Example 10.

Monolithic and core-type pellets of the invention were made with the active methocarbamol, an antispasmodic agent with a melting point of 93° C. (obtained from VWR). As in Example 9, monolithic pellets were prepared as described in General Procedure A, containing 85 wt. % methocarbamol, 12 wt. % cholesterol, and 3 wt. % phosphatidylcholine. Core-type pellets were prepared as described in General Procedure B, with a shell of 97 wt. % cholesterol and 3 wt. % phosphatidylcholine, and a core composition of 100% methocarbamol fed into the shell during pellet manufacture. As in Example 9, monoliths and core-type pellets were 2.8 mm in diameter, with monoliths 5.5 mm in length and core-type pellets 4 mm in length. Methocarbamol release from both pellet types was evaluated; results are shown in FIG. 22. As with the naproxen monoliths and core-type pellets in the preceding example, FIG. 22 indicates that the methocarbamol core pellet provided approximately zero-order release, while the methocarbamol monolith gave a release profile in which release rate decreased approximately linearly until the drug was depleted.

Examples 11 and 12

Cholecalciferol and Acetaminophen Pellets

Figure 23:
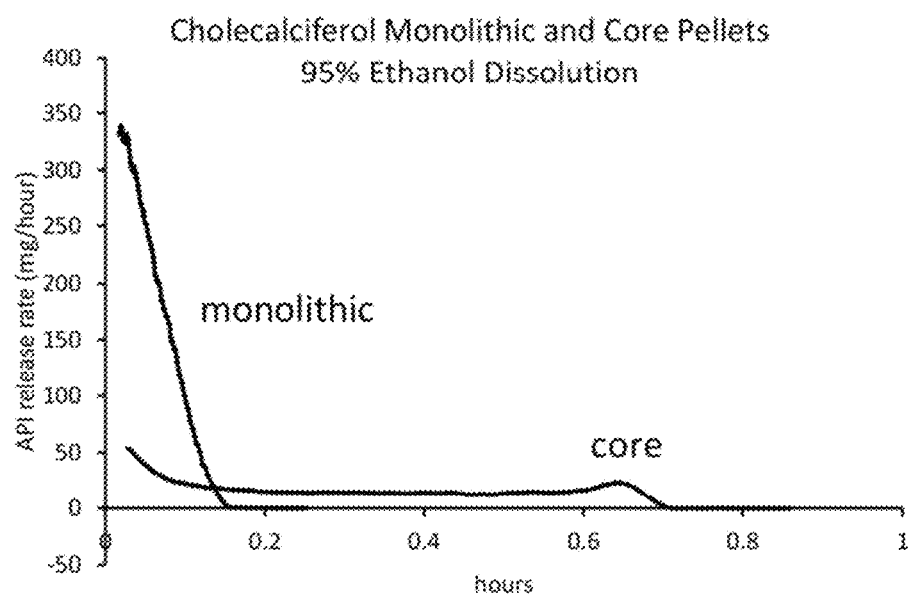
Figure 24:
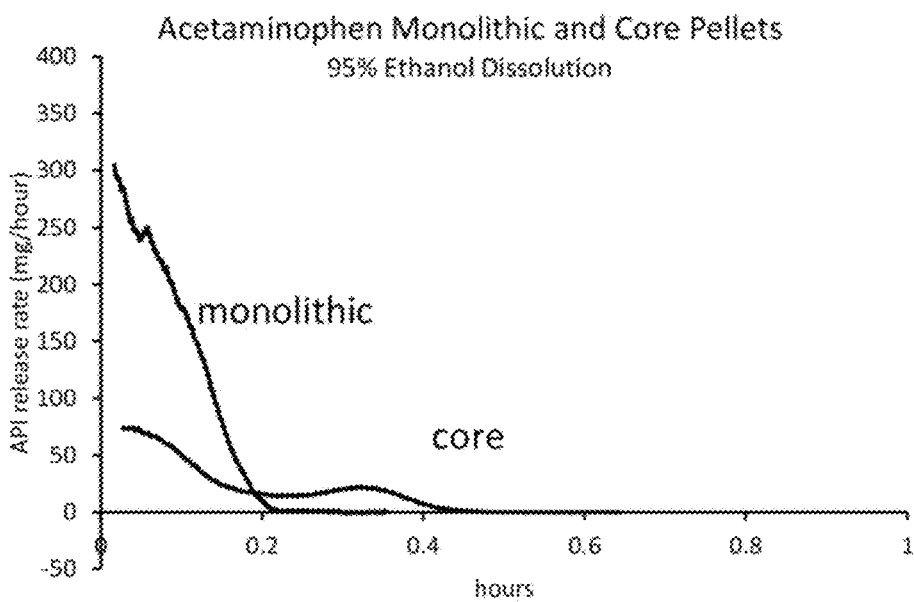
FIG. 24 shows the dissolution of monolithic pellets and core-type pellets made with acetaminophen, as described in Example 12.

The procedures of Examples 9 and 10 were repeated to prepare analogous monolithic and core-type pellets with cholecalciferol (Vitamin D$_3$, melting point 84.5° C.) (Example 11) and acetaminophen (melting point 168° C.) (Example 12), both active agents obtained from VWR. Drug release was evaluated in Examples 9 and 10, with results shown in FIG. 23, for cholecalciferol, and FIG. 24, for acetaminophen.

Figure 25:
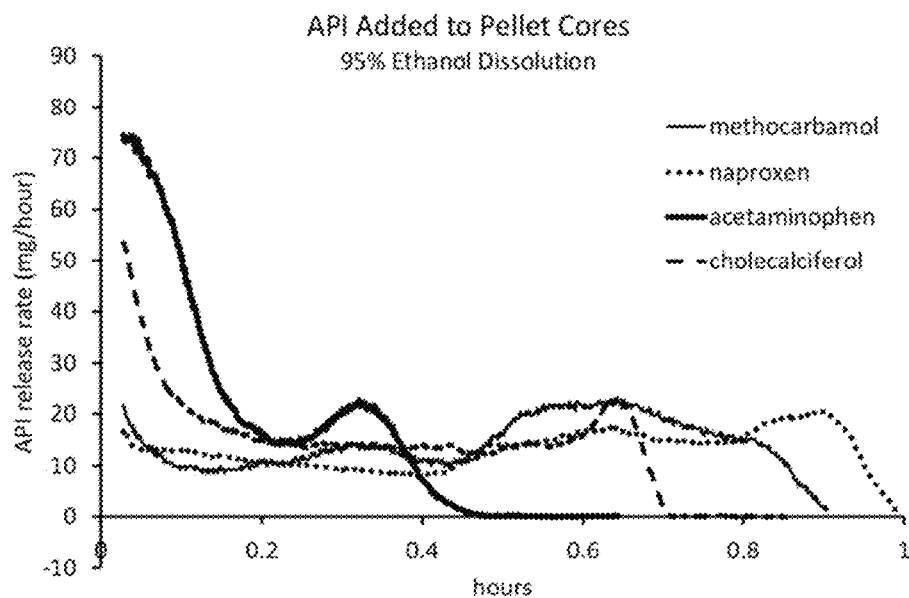
Figure 26:
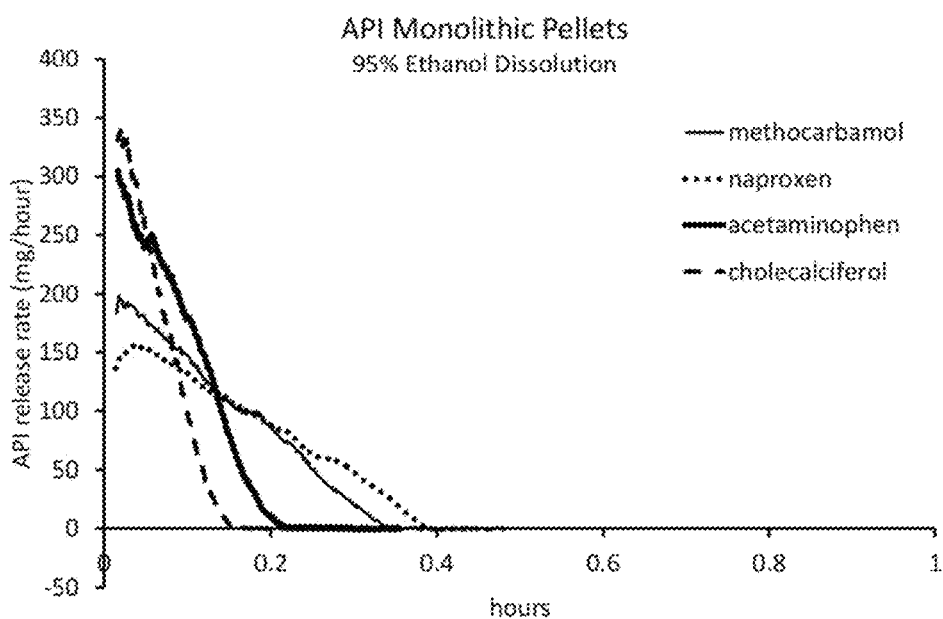
FIG. 26 shows the release profiles for the corresponding monolithic pellets prepared in Examples 9-12.

In FIG. 25, the release profiles are plotted for each of the core pellets prepared in Examples 9-12, i.e., for naproxen, methocarbamol, cholecalciferol, and acetaminophen, while FIG. 26 shows the release profiles for the corresponding monolithic pellets.

Active agent release rates and release profiles with the present drug delivery systems depend on several factors including water solubility, crystallinity melting point (i.e., stability of crystalline form), and active agent-excipient interactions that may alter solubility and/or crystalline stability. The results in Examples 9-12 indicate that, as a general trend, faster release from the monolithic pellets correlates with faster release from the core pellet with the same active agent. However, the correlation is not absolute, presumably because each active agent interacts differently with the excipient composition in the monolithic pellets that is not present in the core material.

It should also be noted that active agent release from monolithic pellets is relatively high at the beginning and tapers off, while active agent release from the core-type pellets is relatively stable over the duration of drug release. Either type of pellet may be preferred, depending on the particular active agent.

We claim:

1. A method for making a core-and-shell type of pellet for controlled release of a pharmacologically active agent, the method comprising:
   (a) providing (i) an elongated pin comprising two axially aligned, substantially cylindrical adjacent segments of different diameters, with a wider lower segment and a narrower upper segment that terminates in a pin tip, (ii) a pelleting tube having an upper tube opening, an opposing lower tube opening, an inner surface, and an inner diameter sized to provide a sealing fit between the inner surface and the lower segment of the pin, and (iii) a funnel having an outlet aligned with the upper tube opening;
   (b) inserting the pin tip into the lower tube opening and moving the pin upward through the tube toward the funnel until the pin tip and upper pin segment protrude from the upper tube opening into the funnel, thereby bringing the lower segment within the tube;
   (c) placing a molten shell composition in the funnel;
   (d) gradually withdrawing the lower segment from the tube, thereby lowering the upper segment into the tube and simultaneously drawing the shell composition into a concentric space between the upper segment and the inner surface of the tube;
   (e) allowing the shell composition to cool and thereby harden into a shell formed around the upper segment within the concentric space;
   (f) placing a molten core composition into the funnel; and
   (g) gradually lowering the upper segment within the tube, thereby drawing the core composition into the shell to form a core,
   wherein the shell composition and/or core composition contain a pharmacologically active agent.

2. The method of claim 1, wherein the pharmacologically active agent is in the shell composition and not in the core composition.

3. The method of claim 1, wherein the pharmacologically active agent is in the core composition and not in the shell composition.

4. The method of claim 1, wherein at least about 80 wt. % of the pharmacologically active agent in the pellet is in the core.

5. The method of claim 1, wherein at least about 80 wt. % of the pharmacologically active agent in the pellet is in the shell.

6. The method of claim 1, wherein the core and the shell each contain at least about 20 wt. % of the pharmacologically active agent in the pellet.

7. The method of claim 1, wherein the core contains a first pharmacologically active agent and the shell contains a second pharmacologically active agent.

8. The method of claim 1, wherein the pharmacologically active agent has an aqueous solubility of less than about 50 mg/mL.

9. The method of claim 1, wherein the active agent comprises an analgesic agent; an anti-anxiety agent; an anti-arthritic agent; an anti-asthmatic agent; an anticancer agent; an anticholinergic agent; an anticholinesterase; an anticonvulsant; an antidepressant; an antidiabetic agent; an antidiarrheal agent; an anti-emetic agent; an antihistamine; an antihyperlipidemic agent; an anti-infective agent; an anti-inflammatory agent; an antimigraine agent; an anti-obesity agent; an antipruritic agent; an antipsychotic agent; an antispasmodic agent; an agent for treating a neurodegenerative disease; a cardiovascular medicament; a diuretic agent; a gastrointestinal medication; a hormone; an anti-hormone; a hypnotic agent; an immunosuppressive agent; a leukotriene inhibitor; a narcotic agonist or antagonist; a neurotransmitter; nicotine; a nucleic acid; a peptide drug; a nutrient; a sympathomimetic agent; a thrombolytic agent; a vasodilator; or a combination thereof.

10. The method of claim 9, wherein the pharmacologically active agent comprises an antipsychotic agent.

11. The method of claim 9, wherein the pharmacologically active agent comprises an anti-inflammatory agent.

12. The method of claim 11, wherein the anti-inflammatory agent is a nonsteroidal anti-inflammatory agent.

13. The method of claim 9, wherein the pharmacologically active agent comprises a gastrointestinal medication.

14. The method of claim 13, wherein the gastrointestinal medication is a proton pump inhibitor.

15. The method of claim 9, wherein the active agent comprises an anticancer agent.

16. The method of claim 15, wherein the anticancer agent is selected from an anti-metabolite, an anti-microtubule agent, a cytotoxic antibiotic, a topoisomerase inhibitor, an aromatase inhibitor, a GnRH analogue, a hormone receptor antagonist, a hormonal agent, an anti-angiogenic agent, an anti-metastatic agent, and a combination thereof.

17. The method of claim 9, wherein the active agent comprises an anti-infective agent.

18. The method of claim 17, wherein the anti-infective agent is selected from an antibiotic, an antiviral agent, an antifungal agent, an antiparasitic agent, and a combination thereof.

19. The method of claim 9, wherein the active agent comprises a cardiovascular medicament.

20. The method of claim 9, wherein the cardiovascular medicament is selected from an antiarrhythmic agent, an antihypertensive agent, an anti-anginal agent, and a combination thereof.

21. The method of claim 9, wherein the active agent comprises an anti-convulsant agent.

22. The method of claim 9, wherein the active agent comprises an agent for treating a neurodegenerative disorder.

23. The method of claim 9, wherein the active agent comprises a hormone.

24. The method of claim 23, wherein the hormone comprises a steroid.

25. The method of claim 9, wherein the active agent comprises a nutrient.

26. The method of claim 25, wherein the nutrient comprises a vitamin.

27. The method of claim 1, wherein the shell, the core, or both the shell and core comprise an excipient composition.

28. The method of claim 27, wherein the excipient composition is lipophilic.

29. The method of claim 28, wherein the excipient composition comprises a sterol ester.

\* \* \* \* \*